US010464964B2

(12) United States Patent
Zetterberg et al.

(10) Patent No.: US 10,464,964 B2
(45) Date of Patent: Nov. 5, 2019

(54) GALACTOSIDE INHIBITOR OF GALECTINS

(71) Applicant: Galecto Biotech AB, Copenhagen (DK)

(72) Inventors: Fredrik Zetterberg, Askim (SE); Ulf Nilsson, Lund (SE); Hakon Leffler, Lund (SE); Thomas Brimert, Blentarp (SE); Richard Johnsson, Lund (SE); Priya Verma, Uttar Pradesh (IN)

(73) Assignee: Galecto Biotech AB, Copenhagen (DK)

( * ) Notice: Subject to any disclaimer, the term of this patent is extended or adjusted under 35 U.S.C. 154(b) by 195 days.

(21) Appl. No.: 15/535,837

(22) PCT Filed: Jan. 14, 2016

(86) PCT No.: PCT/EP2016/050633
§ 371 (c)(1),
(2) Date: Jun. 14, 2017

(87) PCT Pub. No.: WO2016/113335
PCT Pub. Date: Jul. 21, 2016

(65) Prior Publication Data
US 2017/0334940 A1 Nov. 23, 2017

(30) Foreign Application Priority Data
Jan. 16, 2015 (EP) .................................... 15151414

(51) Int. Cl.
*C07H 19/056* (2006.01)
*C07H 3/04* (2006.01)

(52) U.S. Cl.
CPC ............. *C07H 19/056* (2013.01); *C07H 3/04* (2013.01)

(58) Field of Classification Search
None
See application file for complete search history.

(56) References Cited

U.S. PATENT DOCUMENTS

2014/0121179 A1* 5/2014 Henderson ............ A61M 15/00
514/53

FOREIGN PATENT DOCUMENTS

WO 2009/139719 A1 11/2009
WO 2014/078655 A1 5/2014

OTHER PUBLICATIONS

Jenny Almkvist, et al., "Lipopolysaccharide-Induced Gelatinase Granule Mobilization Primes Neutrophils for Activation by Galectin-3 and Formylmethionyl-Leu-Phe", in Infection and Immunity, vol. 69, No. 2, Feb. 2001, pp. 832-837 (6 pgs.).
Samuel H. Barondes, et al., "Galectins", in The Journal of Biological Chemistry, vol. 269, No. 33, Aug. 19, 1994, pp. 20807-20810 (4 pgs.).
Sandra M. Blois, et al., "A pivotal role for galectin-1 in fetomaternal tolerance", in Nature Medicine, vol. 13, No. 12, Dec. 2007, pp. 1450-1457 (8 pgs.).
W-S. Chen, et al., "Targeting Galectin-1 and Galectin-3 Attenuates VEGF-A-induced Angiogenesis", in Molecular Biology Cell (suppl), Abstract, No. 2695, 2012, (1 pg.).
Ian Cumpstey, et al., "Synthesis of a phenyl thio-β-D-galactopyranoside library from 1,5-difluoro-2,4-dinitrobenzene: discovery of efficient and selective monosaccharide inhibitors of galectin-7", in Org. Biomol. Chem., vol. 3, 2005, pp. 1922-1932 (11 pgs.).
Ian Cumpstey, et al., "C2-Symmetrical thiodigalactoside bis-benzamido derivatives as high-affinity inhibitors of galectin-3: Efficient lectin inhibition through double arginine-arene interactions", in Angew. Chem. Int., Ed. 44, 2005, pp. 5110-5112 (3 pgs.).
Ian Cumpstey, et al., "Double Affinity Amplification of Galectin-Ligand Interactions through Arginine-Arene Interactions: Synthetic, Thermodynamic, and Computational Studies with Aromatic Diamido Thiodigalactosides", in Chem. Eur. J., vol. 14, 2008, pp. 4233-4245 (13 pgs.).
T. K. Dam, et al., "Effects of Clustered Epitopes in Multivalent Ligand-Receptor Interactions", in Biochemistry, vol. 47, 2008, pp. 8470-8476 (7 pgs.).
D. Delacour, et al., "Apical Sorting by Galectin-3-Dependent Glycoprotein Clustering", in Traffic, vol. 8, 2007, pp. 379-388 (10 pgs.).
T. Delaine, et al., "Galectin-Inhibitory Thiodigalactoside Ester Derivatives Have Antimigratory Effects in Cultured Lung and Prostate Cancer Cells", in J. Med. Chem., vol. 51, 2008, pp. 8109-8114 (6 pgs.).
O. B. Garner, et al., "Galectin-glycan lattices regulate cell-surface glycoprotein organization and signalling", in Biochemical Society Transactions, vol. 36, Part 6, 2008, pp. 1472-1477 (6 pgs.).
D. Giguère, et al., "Carbohydrate triazoles and isoxazoles as inhibitors of galectins-1 and -3", in Chem. Commun., 2006, pp. 2379-2381 (3 pgs.).
G. V. Glinsky, et al., "Inhibition of Human Breast Cancer Metastasis in Nude Mice by Synthetic Glycoamines1", in Cancer Research, vol. 56, Dec. 1, 1996, pp. 5319-5324 (6 pgs.).
V. V. Glinsky, et al., "Synthetic Galectin-3 Inhibitor Increases Metastatic Cancer Cell Sensitivity to Taxol-Induced Apoptosis in Vitro and in Vivo1", in Neoplasia, vol. 11, No. 9, Sep. 2009, pp. 901-909 (9 pgs).
M. E. Huflejt, et al., "Galectin-4 in normal tissues and cancer", in Glycoconjugate Journal 20, 2004, pp. 247-255 (9 pgs.).
L. Ingrassia, et al., "A Lactosylated Steroid Contributes in Vivo Therapeutic Benefits in Experimental Models of Mouse Lymphoma and Human Glioblastoma", in J. Med. Chem., vol. 49, 2006, pp. 1800-1807 (8 pgs.).
C. M. John, et al., "Truncated Galectin-3 Inhibits Tumor Growth and Metastasis in Orthotopic Nude Mouse Model of Human Breast Cancer1", in Clinical Cancer Research, vol. 9, Jun. 2003, pp. 2374-2383 (10 pgs.).

(Continued)

*Primary Examiner* — Traviss C McIntosh, III
(74) *Attorney, Agent, or Firm* — Maier & Maier, PLLC

(57) ABSTRACT

An Embodiment of the invention relates to a compound of the general formula. The compound of formula is suitable for use in a method for treating a disorder relating to the binding of a galectin, such as galectin-3 to a ligand in a mammal, such as a human. Furthermore an embodiment of the present invention concerns a method for treatment of a disorder relating to the binding of a galectin, such as galectin-3 to a ligand in a mammal, such as a human.

20 Claims, No Drawings

(56) References Cited

OTHER PUBLICATIONS

K. S. Lau, et al., "N-Glycans in cancer progression", in Glycobiology, vol. 18, No. 10, 2008, pp. 750-760 (11 pgs.).
K. S. Lau, et al., "Complex N-Glycan Number and Degree of Branching Cooperate to Regulate Cell Proliferation and Differentiation", in Cell 129, Apr. 6, 2007, pp. 123-134 (12 pgs.).
H. Leffler, et al., "Specificity of Binding of Three Soluble Rat Lung Lectins to Substituted and Unsubstituted Mammalian 3-Galactosides", in The Journal of Biological Chemistry, vol. 261, No. 22, Aug. 5, 1986, pp. 10119-10126 (8 pgs.).
H. Leffler, "Galectins Structure and Function—A Synopsis", in Results and Problems in Cell Differentiation, vol. 33, 2001, pp. 57-83 (27 pgs.).
H. Leffler, et al., "Introduction to galectins", in Glycoconjugate Journal 19, 2004, pp. 433-440 (8 pgs.).
Chi-lou Lin, et al., "Galectin-3 Targeted Therapy with a Small Molecule Inhibitor Activates Apoptosis and Enhances Both Chemosensitivity and Radiosensitivity in Papillary Thyroid Cancer", in Mol. Cancer Res., vol. 7, No. 10, Oct. 2009, pp. 1655-1662 (8 pgs.).
A. C. MacKinnon, et al., "Regulation of Alternative Macrophage Activation by Galectin-3", in The Journal of Immunology, vol. 180, pp. 2650-2658 (9 pgs.).
A. C. MacKinnon, et al., "Regulation of Transforming Growth Factor-$\beta$1-driven Lung Fibrosis by Galectin-3", in American Journal of Respiratory and Critical Care Medicine, vol. 185, 2012, pp. 1-10 (11 pgs.).
S. M. Massa, et al., "L-29, an Engogenous Lectin, Binds to Glycoconjugate Ligands with Positive Cooperativity", in Biochemistry, vol. 32, 1993, pp. 260-267 (8 pgs.).
I. Melero, et al., "Evolving synergistic combinations of targeted immunotherapies to combat cancer", in Nature Reviews Cancer, vol. 15, Aug. 2015, pp. 457-472 (16 pgs.).
E. A. Partridge, et al., "Regulation of Cytokine Receptors by Golgi N-Glycan Processing and Endocytosis", in Science, vol. 306, Oct. 1, 2004, pp. 120-124 (6 pgs., including cover sheet).
M. J. Perone, et al., "Suppression of Autoimmune Diabetes by Soluble Galectin-1", in The Journal of Immunology, vol. 182, 2009, pp. 2641-2653 (13 pgs.).
K. J. Pienta, et al., "Inhibition of Spontaneous Metastasis in a Rat Prostate Cancer Model by Oral Administration of Modified Citrus Pectin", in the Journal of the National Cancer Institute, vol. 87, No. 5, Mar. 1, 1995, pp. 348-353 (6 pgs.).
J. Saegusa, et al., "Galectin-3 Is Critical for the Development of the Allergic Inflammatory Response in a Mouse Model of Atopic Dermatitis", in The American Journal of Pathology, vol. 174, No. 3, Mar. 2009, pp. 922-931 (10 pgs.).
B. A. Salameh, et al., "3-(1,2,3-Triazol-1-yl)-1-thio-galactosides as small, efficient, and hydrolytically stable inhibitors of galectin-3", in Biorganic & Medicinal Chemistry Letters, vol. 15, 2005, pp. 3344-3346 (3 pgs.).
B. A. Salameh, et al., "1H-1,2,3-Triazol-1-yl thiodigalactoside derivatives as high affinity galectin-3 inhibitors", in Bioorganic & Medicinal Chemistry, vol. 18, 2010, pp. 5367-5378 (13 pgs.).
E. Salomonsson, et al., "Monovalent Interactions of Galectin-1", in Biochemistry, vol. 49, 2010, pp. 9518-9532 (15 pgs.).
P. Sörme, et al., "Low Micromolar Inhibitors of Galectin-3 Based on 3'-Derivatizatoin of N-Acetyllactosamine", in ChemBioChem, vol. 3, 2002, pp. 183-189 (7 pgs.).
P. Sörme, et al., "Fluorescence Polarization to Study Galectin-Ligand Interactions", in Methods of Enzymology, vol. 362, 2003, pp. 504-512 (9 pgs.).
P. Sörme, et al., "Design and Synthesis of Galectin Inhibitors", in Methods of Enzymology, vol. 363, 2003, pp. 157-169 (13 pgs.).
P. Sörme, et al., "Fluorescence polarization as an analytical tool to evaluate galectin-ligand interactions", in Analytical Biochemistry, vol. 334, 2004, pp. 36-47 (12 pgs.).

V.L.J.L. Thijssen, et al., "Galectins in the tumor endothelium: opportunities for combined cancer therapy", in Blood, vol. 110, 2007, pp. 2819-2827 (10 pgs.).
M. A. Toscano, et al., "Differential glycosylation of TH1, TH2 and TH-17 effector cells selectively regulates susceptibility to cell death", in Nature Immunology, vol. 8, No. 8, Aug. 2007, pp. 825-834 (10 pgs.).
G. A. Rabinovich, et al., "Shedding light on the immunomodulatory properties of galectins: Novel regulators of innate and adaptive immune responses", in Glycoconjugate Journal 19, 2004, pp. 565-573 (9 pgs.).
Lorenzo Chiariotti, et al., "Galectin genes: Regulation of expression", in Glycoconjugate Journal 19, 2004, pp. 441-449 (9 pgs.).
Tomohisa Ogawa, et al., "The speciation of conger eel galectins by rapid adaptive evolution", in Glycoconjugate Journal 19, 2004, pp. 451-458 (8 pgs.).
C. Fred Brewer, "Thermodynamic binding studies of galectin-1, -3 and -7", in Glycoconjugate Journal 19, 2004, pp. 459-465 (7 pgs.).
Ken Scott, et al., "Galectin-1: A bifunctional regulator of cellular proliferation", in Glycoconjugate Journal 19, 2004, pp. 467-477 (11 pgs.).
Hidenori Horie, et al., "Galectin-1 plays essential roles in adult mammalian nervous tissues. Roles of oxidized galectin-1", in Glycoconjugate Journal 19, 2004, pp. 479-489 (11 pgs.).
Michael S. Lipkowitz, et al., "Galectin 9 is the sugar-regulated urate transporter/channel UAT", in Glycoconjugate Journal 19, 2004, pp. 491-498 (8 pgs.).
Ronald J. Patterson, et al., "Understanding the biochemical activities of galectin-1 and galectin-3 in the nucleus", in Glycoconjugate Journal 19, 2004, pp. 499-506 (8 pgs.).
Daniel K. Hsu, et al., "Regulation of cellular homeostasis by galectins", in Glycoconjugate Journal 19, 2004, pp. 507-515 (9 pgs.).
Yehiel Zick, et al., "Role of galectin-8 as a modulator of cell adhesion and cell growth", in Glycoconjugate Journal 19, 2004, pp. 517-526 (10 pgs.).
International Search Report issued in corresponding PCT/EP2016/050633 dated Mar. 2, 2016; 3 pgs.
Josiah Ochieng, et al., "Extracellular functions of galectin-3", in Glycoconjugate Journal 19, 2004, pp. 527-535 (9 pgs.).
Frèdèric van den Brûle, et al., "Expression of galectins in cancer: A critical review", in Glycoconjugate Journal 19, 2004, pp. 537-542 (6 pgs.).
Yukinori Takenaka, et al., "Galectin-3 and metastasis", in Glycoconjugate Journal 19, 2004, pp. 543-549 (7 pgs.).
Antonin Grassadonia, et al., "90K (Mac-2 BP) and galectins in tumor progression and metastasis", in Glycoconjugate Journal 19, 2004, pp. 551-556 (6 pgs.).
Nathalie Bidon-Wagner, et al., "Human galectin-8 isoforms and cancer", in Glycoconjugate Journal 19, 2004, pp. 557-563 (7 pgs.).
Jenny Almkvist, et al., "Galectins as inflammatory mediators", in Glycoconjugate Journal 19, 2004, pp. 575-581 (7 pgs.).
Sachiko Sato, et al., "Seeing strangers or announcing "danger": Galectin-3 in two models of innate immunity", in Glycoconjugate Journal 19, 2004, pp. 583-591 (9 pgs.).
Mitsuomi Hirashima, et al., "Galectin-9 in physiological and pathological conditions", in Glycoconjugate Journal 19, 2004, pp. 593-600 (8 pgs.).
Anna R. Young, et al., "Galectins in parasite infection and allergic inflammation", in Glycoconjugate Journal 19, 2004, pp. 601-606 (6 pgs.).
Karen E. Pace, et al., "Insect galectins: Roles in immunity and development", in Glycoconjugate Journal 19, 2004, pp. 607-614 (8 pgs.).
Diana J. Watt, et al., "The involvement of galectin-1 in skeletal muscle determination, differentiation and regeneration", in Glycoconjugate Journal 19, 2004, pp. 615-619 (5 pgs.).
R. Colin Hughes, "Galectins in kidney development", in Glycoconjugate Journal 19, 2004, pp. 621-629 (9 pgs.).

\* cited by examiner

GALACTOSIDE INHIBITOR OF GALECTINS

TECHNICAL FIELD

The present relates to novel compounds, the use of said compounds as medicament and for the manufacture of a medicament for the treatment of inflammation; fibrosis; scarring; keloid formation; aberrant scar formation; surgical adhesions; septic shock; cancer; metastasising cancers; autoimmune diseases; metabolic disorders; heart disease; heart failure; pathological angiogenesis; eye diseases; atherosclerosis; metabolic diseases; asthma and other intestinal lung disease; liver disorders in mammals. The invention also relates to pharmaceutical compositions comprising said novel compounds.

BACKGROUND ART

Galectins are proteins with a characteristic carbohydrate recognition domain (CRD) (Barondes et al., 1994; Leffler et al., 2004). This is a tightly folded β-sandwich of about 130 amino acids (about 15 kDa) with the two defining features 1) a β-galactose binding site and 2) sufficient similarity in a sequence motif of about seven amino acids, most of which (about six residues) make up the β-galactose binding site. However, sites adjacent to the β-galactose site are required for tight binding of natural saccharides and different preferences of these give galectins different fine specificity for natural saccharides.

The recent completion of the human, mouse and rat genome sequences reveal about 15 gelectins and galectin-like proteins in one mammalian genome with slight variation between species (Leffler et al., 2004)

Galectin subunits can contain either one or two CRDs within a single peptide chain. The first category, mono-CRDs galectins, can occur as monomers or dimers (two types) in vertebrates. The by far best studied galectins are the dimeric galectin-1, and galectin-3 that is a monomer in solution but may aggregate and become multimeric upon encounter with ligands (Leffler et al., 2004). These were the first discovered galectins and are abundant in many tissues.

There are now over 3500 publications on galectins in PubMed, with most, as mentioned above, about galectins-1 (>900) and -3 (>1600). Strong evidence suggests roles for galectins in e.g. inflammation and cancer, and development recently reviewed in a special issue (Leffler (editor), 2004b).

Galectins are synthesized as cytosolic proteins, without a signal peptide on free ribosomes. Their N-terminus is acetylated, a typical modification of cytosolic proteins, and they reside in the cytosol for a long time (not typical of secreted proteins). From there they can be targeted to the nucleus, specific cytososlic sites, or secreted (induced or constitutively) by a non-classical (non-ER-Golgi) pathway, as yet unknown, but possibly similar to the export of e.g. IL-1 (Leffler et al., 2004). They can also function in all these compartments; for galectin-3, solid evidence published in well respected journals support roles in RNA splicing in the nucleus, inhibition of apoptosis in the cytosol, and a variety of extracellular effects on cell signaling and adhesion (Leffler (editor), 2004b). Galectin-7 and -12 also act in the cytosol by enhancing apoptosis and regulating the cell cycle and differentiation in certain cells (Hsu and Liu in Leffler (editor), 2004b). Most galectins act also extracellularly by cross-linking glycoproteins (e.g. laminin, integrins, and IgE receptors) possibly forming supramolecular ordered arrays (Brewer et al., 2002) and may thereby modulate cell adhesion and induce intracellular signals. Related to this, recent years have seen the emergence of a molecular mechanism of these galectin functions involving a formation of microdomains (lattices) within membranes, (Dam et al., 2008; Garner et al., 2008) which in turn affects intracellular trafficking and cell surface presentation of glycoprotein receptors. (Delacour et al., 2007; Lau et al., 2007; Lau et al. 2008) This has been documented in cell culture, in null mutant mice, (Blois et al., 2007; Gedronneau et al., 2008; Thijssen et al., 2007; Toscano et al., 2007; Saegusa et al., 2009) and animals treated with galectin (Blois et al., 2007; Perone et al., 2009) or galectin inhibitors. (John et al., 2003; Pienta et al., 1995; Glinsky et al., 1996)

Potential Therapeutic Use of Galectin-3 Inhibitors

Galectin-3 has been implicated in diverse phenomena and, hence, inhibitors may have multiple uses. It is easy to perceive this as a lack of specificity of lack of scientific focus. Therefore, the analogy with aspirin and the cyclooxygenases (COX-I and II) is useful. The COXs produce the precursor of a wide variety of prostaglandins and, hence, are involved in a diverse array of biological mechanisms. Their inhibitors, aspirin and other NSAIDs (non-steroid anti-inflammatory drugs), also have broad and diverse effects. Despite this, these inhibitors are very useful medically, and they have several different specific utilities.

So if galectins, like COXs, are part of some basic biological regulatory mechanism (as yet unknown), they are likely to be 'used by nature' for different purpose in different contexts. Galectin inhibitors, like NSAIDs, are not expected to wipe out the whole system, but to tilt the balance a bit.

Inhibition of Inflammation

A pro-inflammatory role of galectin-3 is indicated by its induction in cells at inflammatory sites, a variety of effects on immune cells (e.g. oxidative burst in neutrophils and chemotaxis in monocytes), and decrease of the inflammatory response, mainly in neutrophils and macrophages, in null mutant mice (in Leffler (editor), 2004b). Moreover, knock-out mice of Mac-2BP, a galectin-3 ligand, have increased inflammatory responses (Trahey et al., 1999). Importantly, recent studies have identified galectin-3 as a key rate-limiting factor in macrophage M2 differentiation of myofibroblast activation, which influences the development of fibrosis (Mackinnon et al., 2008; Mackinnon et al., 2012).

Inflammation is a protective response of the body to invading organisms and tissue injury. However, if unbalanced, frequently it is also destructive and occurs as part of the pathology in many diseases. Because of this, there is great medical interest in pharmacological modulation of inflammation. A galectin-3 inhibitor is expected to provide an important addition of the arsenal available for this.

Treatment of Fibrosis-Related Conditions

The idea of a possible role of galectin-3 in fibrosis comes from cell and ex vivo studies on macrophage differentiation (Mackinnon et al., 2008), as well as from in vivo studies on macrophage differentiation and myofibroblast activation (Mackinnon et al., 2012). Briefly, the hypothesis is as follows: Galectin-3 has been shown to prolong cell surface residence and thus enhance responsiveness of the TGF-β receptor (Partridge et al., 2004), which in turn regulates alternative macrophage differentiation into M2 macrophages and myofibroblast activation.

Hence, as galectin-3 is a good candidate for being an endogenous enhancer of TGF-β signaling and alternative macrophage differentiation and myofibroblast activation, galectin-3 inhibitors may be very useful in treating fibrosis and adverse tissue remodeling.

Treatment of Cancer

A large number of immunohistochemical studies show changed expression of certain galectins in cancer (van den Brule et. al. and Bidon et al. in Leffler (2004b) and for example galectin-3 is now an established histochemical marker of thyroid cancer. The direct evidence for a role of galectin-3 in cancer comes from mouse models, mainly by Raz et al, but also others (in Leffler (editor), 2004b). In paired tumor cell lines (with decreased or increased expression of galectin-3), the induction of galectin-3 gives more tumors and metastasis and suppression of galectin-3 gives less tumors and metastasis. Galectin-3 has been proposed to enhance tumor growth by being anti-apoptotic, promote angiogenesis, or to promote metastasis by affecting cell adhesion. From the above it is clear that inhibitors of galectin-3 might have valuable anti-cancer effects. Indeed, saccharides claimed but not proven to inhibit galectin-3 have been reported to have anti-cancer effects. In our own study a fragment of galectin-3 containing the CRD inhibited breast cancer in a mouse model by acting as a dominant negative inhibitor (John et al., 2003). More recently, inhibition of galectin-3 with small molecules have been demonstrated to indeed greatly enhance tumor cell sensitivity towards radiation and standard pro-apoptotic drugs in cell assays and ex vivo (Lin et al., 2009), as well as in vivo (Glinsky et al., 2009).

Also galectin-1 is frequently over-expressed in low differentiated cancer cells, and galectin-9 or its relatives galectin-4 and galectin-8 may be induced in specific cancer types (Huflejt and Leffler, 2004; Leffler (editor), 2004b). Galectin-1 induces apoptosis in activated T-cells and has a remarkable immunosuppressive effect on autoimmune disease in vivo (Rabinovich et al; and Pace et al. in Leffler (editor), 2004b). Therefore, the over-expression of these galectins in cancers might help the tumor to defend itself against the T-cell response raised by the host.

Null mutant mice for galectins-1 and -3 have been established many years ago (Poirier, 2002). These are healthy and reproduce apparently normally in animal house conditions. However, recent studies have revealed subtle phenotypes in function of neutrophils and macrophages (as described above) and in bone formation for galectin-3 null mutants, and in nerve and muscle cell regeneration/differentiation for the galectin-1 null mutants (Leffler et al., 2004; Poirier, 2002; Watt in Leffler (editor), 2004b). Recently galectin-7 and galectin-9 null mutant mice have been generated and are also grossly healthy in animal house conditions, but have not yet been analyzed in detail. The differences in site of expression, specificity and other properties make it unlikely that different galectins can replace each other functionally. The observations in the null mutant mice would indicate that galectins are not essential for basic life supporting functions as can be observed in normal animal house conditions. Instead they may be optimizers of normal function and/or essential in stress conditions not found in animal house conditions. The lack of strong effect in null mutant mice may make galectin inhibitors more favorable as drugs. If galectin activity contributes to pathological conditions as suggested above but less to normal conditions, then inhibition of them will have less unwanted side effects.

Treatment of Angiogenesis

Vascular endothelial growth factors (VEGFs) signaling through VEGF receptor-2 (VEGFR-2) is the primary angiogenic pathway. Studies have been published demonstrating that both galectin-1 (Gal-1) and galectin-3 (Gal-3) are important modulators for VEGF/VEGFR-2 signaling pathway. It has also been published that a galectin inhibitor, TDX, is expected have efficacy against pathological angiogenesis. (Chen 2012)

Known Inhibitors
Natural Ligands

Solid phase binding assays and inhibition assays have identified a number of saccharides and glycoconjugates with the ability to bind galectins (reviewed by Leffler, 2001 and Leffler et al., 2004). All galectins bind lactose with a $K_d$ of 0.5-1 mM. The affinity of D-galactose is 50-100 times lower. N-Acetyllactosamine and related disaccharides bind about as well as lactose, but for certain galectins, they can bind either worse or up to 10 times better. The best small saccharide ligands for galectin-3 were those carrying blood group A-determinants attached to lactose or LacNAc-residues and were found to bind up to about 50 times better than lactose. Galectin-1 shows no preference for these saccharides.

Larger saccharides of the polylactosamine type have been proposed as preferred ligands for galectins. In solution, using polylactosamine-carrying glycopeptides, there was evidence for this for galectin-3, but not galectin-1 (Leffler and Barondes, 1986). A modified plant pectin polysaccharide has been reported to bind galectin-3 (Pienta et al., 1995).

The above-described natural saccharides that have been identified as galectin-3 ligands are not suitable for use as active components pharmaceutical compositions, because they are susceptible to acidic hydrolysis in the stomach and to enzymatic degradation. In addition, natural saccharides are hydrophilic in nature, and are not readily absorbed from the gastrointestinal tract following oral administration.

Galectin Specificity

The studies of galectin specificity using inhibition by small natural saccharides mentioned above indicated that all galectins bound lactose, LacNAc and related disaccharides, but that galectin-3 bound certain longer saccharides much better (Leffler and Barondes, 1986). These longer saccharides were characterized by having an additional sugar residue added to the C-3 position of galactose (in e.g. lactose or LacNAc) that bound an extended binding groove. The shape of this groove varies between galectins, suggesting that the same extensions would not be bound equally by the different galectins.

Synthetic Inhibitors

Saccharides coupled to amino acids with anti-cancer activity were first identified as natural compounds in serum, but subsequently, synthetic analogues have been made (Glinsky et al., 1996). Among them, those with lactose or galactose coupled to the amino acid inhibit galectins, but only with about the same potency as the corresponding underivatized sugar. A chemically modified form of citrus pectin (Platt and Raz, 1992) that inhibits galectin-3 shows anti-tumor activity in vivo (Pienta et al., 1995; Nangia-Makker et al., 2002).

Cluster molecules having up to four lactose moieties showed a strong multivalency effect when binding to galectin-3, but not to galectin-1 and galectin-5 (Vrasidas et al., 2003). Cyclodextrin-based glycoclusters with seven galactose, lactose, or N-acetyllactosamine residues also showed a strong multivalency effect against galectin-3, but less so against galectins-1 and -7 (André et al., 2004). Starburst dendrimers (André et al., 1999) and glycopolymers (Pohl et al., 1999; David et al., 2004), made polyvalent in lactose-residues, have been described as galectin-3 inhibitors with marginally improved potency as compared to lactose. The aforementioned synthetic compounds that have been identified as galectin-3 ligands are not suitable for use as active components in pharmaceutical compositions, because they are hydrophilic in nature and are not readily absorbed from the gastrointestinal tract following oral administration.

Natural oligosaccharides, glycoclusters, glycodendrimers, and glycopolymers described above are too polar and too large to be absorbed and in some cases are large enough to produce immune response in patients. Furthermore, they are susceptible to acidic hydrolysis in the stomach and to enzymatic hydrolysis. Thus, there is a need for small synthetic molecules Thiodigalactoside is known to be a synthetic and hydrolytically stable, yet polar inhibitor, approximately as efficient as N-acetyllactosamine (Leffler and Barondes, 1986).

N-Acetyllactosamine derivatives carrying aromatic amides or substituted benzyl ethers at C-3' have been demonstrated to be highly efficient inhibitors of galectin-3, with unprecented IC$_{50}$ values as low as 4.8 µM, which is a 20-fold improvement in comparison with the natural N-acetyllactosamine disaccharide (Sörme et al., 2002; Sörme et al., 2003b). These derivatives are less polar overall, due to the presence of the aromatic amido moieties and are thus more suitable as agents for the inhibition of galectins in vivo. Furthermore, C3-triazolyl galactosides have been demonstrated to be as potent inhibitors as the corresponding C3-amides of some galectins. Hence, any properly structured galactose C3-substituent may confer enhanced galectin affinity.

However, the C3-amido- and C3-triazolyl-derivatised compounds are still susceptible to hydrolytic degradation in vivo, due to the presence of a glycosidic bond in the galactose and N-acetyllactosamine saccharide moiety and, although they are potent small molecule inhibitors of galectin-3, even further improved affinity and stability is desirable. Accordingly, inhibitors based on 3,3'-diamido- or 3,3'-ditriazolyl-derivatization of thiodigalactoside have been developed, (Cumpstey et al., 2005b; Cumpstey et al., 2008; Salameh et al., 2010; WO/2005/113569 and US2007185041; WO/2005/113568, U.S. Pat. No. 7,638,623 B2) which lack O-glycosidic hydrolytically and enzymatically labile linkages. These inhibitors also displayed superior affinity for several galectins (down to Kd in the low nM range). Nevertheless, although displaying high affinity for galectins, the 3,3'-derivatized thiodigalactosides still comprise a disadvantage in their multistep synthesis involving double inversion reaction to reach a 3-N-derivatized galactose building blocks. Furthermore, cyclohexane replacement of one galactose ring in thiodigalactoside has been evidenced to mimic the galactose ring and hence to provide galectin-1 and -3 inhibitors with efficiency approaching those of the diamido- and ditriazolyl-thiodigalactoside derivatives (WO/2010/126435). Replacement of a D-galactopyranose unit with a substituted cyclohexane decreases polarity and most likely also metabolic susceptibility, thus improving drug-like properties.

Some earlier described compounds have the following general formulas

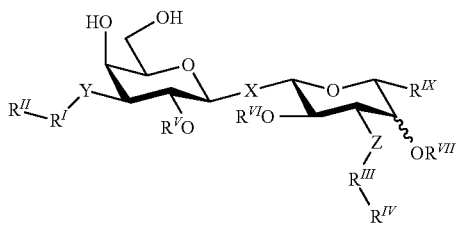

as described in WO/2005/113568, and

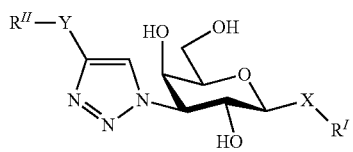

as described in WO/2005/113569, in which R$^I$ can be a D-galactose, and

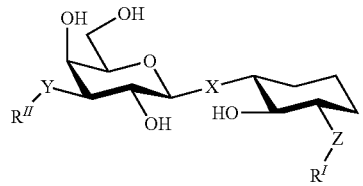

as described in WO/2010/126435.

Thus, due to the less than optimal manufacturing processes towards galactose 3-N-derivatization (Z and Y are preferably nitrogen atoms) involving double inversion reactions at a complex protected D-galactopyranose derivative of the compounds of the prior art, there is still a considered need within the art of inhibitors against galectins, in particular of galectin-1 and galectin-3.

In recently published US20140099319 and WO2014067986 are disclosed a compound of formula

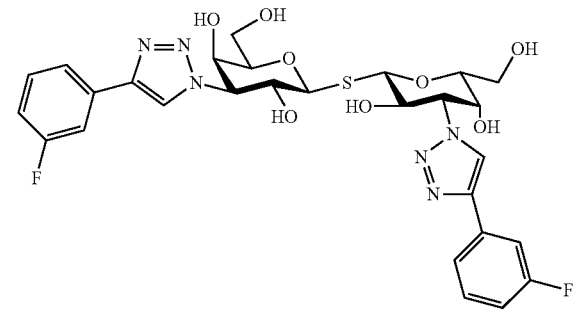

having fluorine in the meta position on both the phenyl rings in relation to the triazole rings. This compound has been shown to be a promising drug candidate for lung fibrosis, and in particular is very selective on galectin-3 with high affinity.

SUMMARY OF THE INVENTION

The compounds of the present invention have very high affinity for Gal-3 and Gal-1, and are considered potent drug candidates. Some of these compounds have high solubility which is important for making pharmaceutical formulations, such as compounds having hetero-cycles with high pKa which can act as a base.

In a broad aspect the present invention relates to a 1,1'-sulfanediyl-di-β-D-galactopyranoside compound of formula (1)

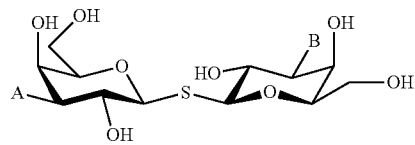

wherein

A is selected from a group of formula 2

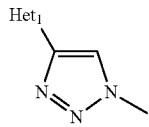

wherein Het1 is selected from a five or six membered heteroaromatic ring, optionally substituted with a group selected from Br, F, Cl, $NH_2$, $NHC(=O)CH_3$, methyl optionally substituted with a F, Oxo (=O), and $OCH_3$ optionally substituted with a F;

B is selected from a group of formula 3, 4 and 5

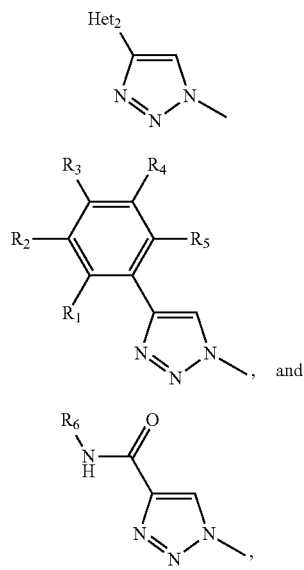

wherein Het2 is selected from a give or six membered heteroaromatic ring, optionally substituted with a group selected from Br, F, Cl, $NH_2$, $NHC(=O)CH_3$, methyl optionally substituted with a F, Oxo, and $OCH_3$ optionally substituted with a F, $R_1$-$R_5$ are independently selected from H, F, methyl optionally substituted with a fluorine (F), and $OCH_3$ optionally substituted with a F, $R_6$ is selected from $C_{1-6}$ alkyl, branched $C_{3-6}$ alkyl and $C_{3-7}$ cycloalkyl; or a pharmaceutically acceptable salt or solvate thereof.

Some of the compounds of the present invention have high solubility, that is above 0.02 mg/ml, and preferably above 0.2 mg/ml, and most preferably above 2 mg/ml, and it is understood that this is in a pharmaceutically relevant composition of excipients. Such compounds are typically a compound of formula (1)

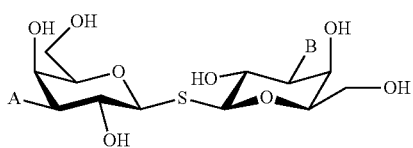

wherein
A is selected from a group of formula 2

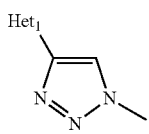

wherein Het1 is selected from a pyridinyl substituted with a group selected from F; and B is selected from a group of formula 3

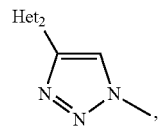

wherein Het2 is selected from a pyridinyl substituted with a group selected from F; or a pharmaceutically acceptable salt or solvate thereof.

Other compounds with high solubility are selected from a compound of formula (1)

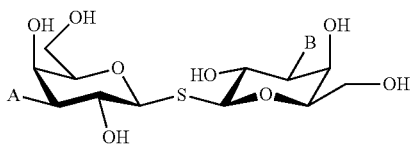

wherein
A is selected from a group of formula 2

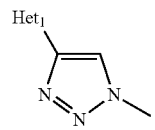

wherein Het1 is selected from a pyridinyl and pyrimidinyl, optionally substituted with a group selected from F, and $NH_2$;

B is selected from a group of formula 4

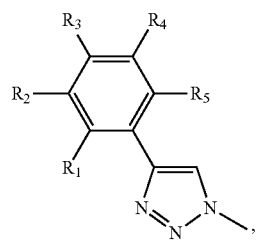

wherein $R_1$-$R_5$ are independently selected from H and F, provided that at least one of $R_2$-$R_4$ is F; or a pharmaceutically acceptable salt or solvate thereof.

In another aspect the present invention relates to a compound of formula (1) for use as a medicine.

In a further aspect the present invention relates to a pharmaceutical composition comprising the compound of formula (1) and optionally a pharmaceutically acceptable additive, such as carrier or excipient.

In a still further aspect the present invention relates to a compound of formula (1) for use in a method for treating a disorder relating to the binding of a galectin, such as galectin-1 and galectin-3 to a ligand in a mammal, such as a human.

In a further aspect the present invention relates to a method for treatment of a disorder relating to the binding of a galectin, such as galectin-1 and galectin-3, to a ligand in a mammal, such as a human, wherein a therapeutically effective amount of at least one compound of formula (1) is administered to a mammal in need of said treatment.

In a still further aspect the present invention relates to a process of preparing a compound of formula 1 or a pharmaceutically acceptable salt or solvate thereof comprising the steps a1:

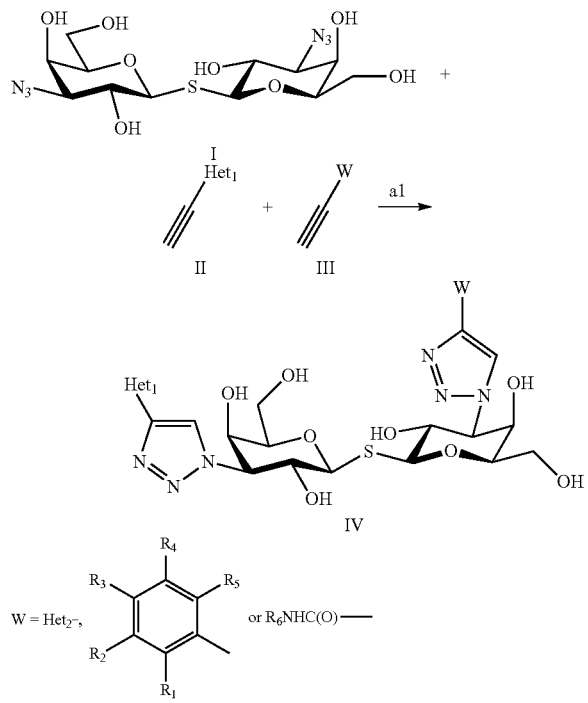

a1) reacting the compound of formula I (which may be obtained as described in WO2009139719) with a compound of formula II and a compound of formula III wherein II=III in an inert solvent, such as DMF, using a base, such as diisopropylamine, catalyzed by CuI to provide the compound of the formula IV wherein A=B. Alternatively when II≠III this reaction could be performed stepwise reacting I with II in an inert solvent, such as DMF, using a base, such as diisopropylamine, catalyzed by CuI. The product of such a reaction is then reacted further with III in an inert solvent, such as DMF, using a base, such as diisopropylamine, catalyzed by CuI to give compounds of formula IV wherein Het$_1$≠W.

In a still further aspect the present invention relates to a process of preparing a compound of formula 1 or a pharmaceutically acceptable salt or solvate thereof comprising the step a2:

a2) reacting the compound of formula V with a compound of formula VI. The sulfur of VI could be unsubstituted or protected as a thiourea, a silyl protective groups, such as Triisopropylsilane (TIPS) or other protective group. When protected as thiourea the coupling could be performed using a weak organic base such as triethylamine. When protected using a silyl protective group in the presence of a reagent, such as tetrabutylammoniumfluoride, the product is then further treated with a base such as sodium methoxide to remove acetate protective groups to provide the compound of formula 1.

In a still further aspect the present invention relates to a process of preparing a compound of formula 1 or a pharmaceutically acceptable salt or solvate thereof comprising the step a3:

a3) reacting I with II in an inert solvent, such as DMF, using a base, such as diisopropylamine, catalyzed by CuI. The product of such a reaction is then reacted further with VII, wherein P1 is selected from $C_{1-5}$ alkyl group, in an inert solvent, such as DMF, using a base, such as diisopropylamine, catalyzed by CuI to give compound which upon treatment with a aliphatic base such as $R_6$—$NH_2$ yields a compound of formula VIII.

In a still further aspect the present invention relates to a process of preparing a compound of formula XI, XII and XIII comprising the steps 14-16;

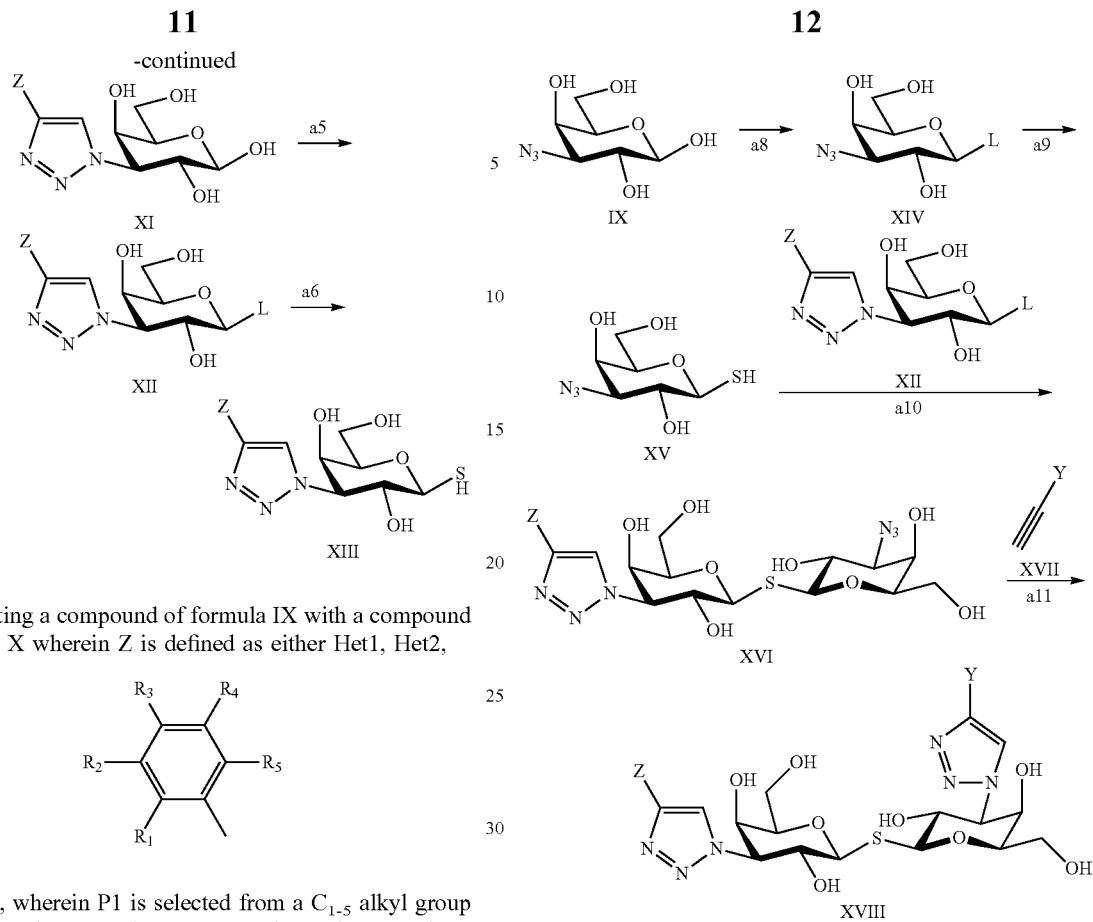

a4) reacting a compound of formula IX with a compound of formula X wherein Z is defined as either Het1, Het2, or COOP1, wherein P1 is selected from a $C_{1-5}$ alkyl group in an inert solvent, such as DMF, using a base, such as diisopropylamine, catalyzed by CuI would provide a compound of formula XI.

a5) Reacting the compound of the formula XI with TiBr4, washing with aqueous $NaHCO_3$ in order to give a compound of the formula XII wherein L is a leaving group, such as Br;

a6) Reacting a compound of the formula XII with triisopropylsilanethiol in an inert solvent, such as acetone, to provide the compound of formula XIII wherein the sulfur is protected with triisopropylsilane; optionally the compound of formula XII could be reacted with thiourea in an inert solvent, such as acetonitrile, optionally at elevated temperatures to give a compound of formula XIII.

In a still further aspect the present invention relates to a process of preparing a compound of formula VI comprising the step a7:

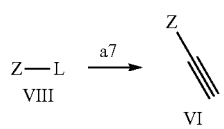

a7) Reacting a compound of formula VIII wherein Z is defined as Het1, Het2, VII or COOP1, wherein P1 is selected from a $C_{1-5}$ alkyl group, such as methyl and L is defined as a leaving group such as bromine, with trimethylsilane-acetylene using a palladium catalyst such as bis(triphenylphosphine)palladium-(II)-chloride and a base like diisopropylamine in an inert solvent, such as THF, to give a compound of formula VI.

In a still further aspect the present invention relates to a process of preparing a compound of formula XVIII comprising the steps a8-a11:

a8) Reacting the compound of the formula IX with a reagent such as TiBr4, washing with aqueous $NaHCO_3$ in order to give a compound of the formula XIV wherein L is a leaving group, such as Br;

a9) Reacting a compound of the formula XIV with triisopropylsilanethiol in an inert solvent, such as acetone, to provide the compound of formula XV wherein the sulfur is protected with triisopropylsilane; optionally the compound of formula XIV could be reacted with thiourea in an inert solvent, such as acetonitrile, optionally at elevated temperatures to give a compound of formula XV.

a10) Reacting the compound of formula XV with a compound of formula XII. The sulfur of XV could be unsubstituted or protected as a thiourea, a silyl protective group, such as Triisopropylsilane (TIPS) or other protective group. When protected as thiourea the coupling could be performed using a weak organic base such as triethylamine. When protected using a silyl protective group in the presence of a reagent, such as tetrabutylammoniumfluoride.

a11) Reacting a compound of formula XVI with a compound of formula XVII wherein Z is defined as either Het1, Het2,

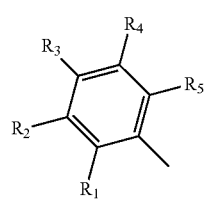

or COOP1, wherein P1 is selected from a $C_{1-5}$ alkyl group in an inert solvent, such as DMF, using a base, such as diisopropylamine, catalyzed by CuI would provide a compound of formula XVIII.

DETAILED DESCRIPTION OF THE INVENTION

In a broad aspect the present invention relates to a 1,1'-sulfanediyl-d-β-D-galactopyranoside compound of formula (1)

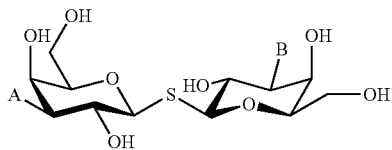

1 wherein
A is selected from a group of formula 2

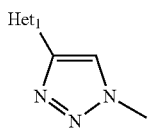

2 wherein Het1 is selected from a five or six membered heteroaromatic ring, optionally substituted with a group selected from Br, F, Cl, $NH_2$, $NHC(=O)CH_3$, methyl optionally substituted with a F, oxo, and $OCH_3$ optionally substituted with a F;

B is selected from a group of formula 3, 4 and 5

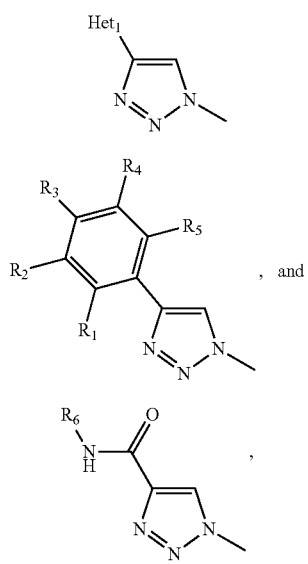

wherein Het2 is selected from a five or six membered heteroaromatic ring, optionally substituted with a group selected from Br, F, Cl, $NH_2$, $NHC(=O)CH_3$, methyl optionally substituted with a F, Oxo, and $OCH_3$ optionally substituted with a F, $R_1$-$R_5$ are independently selected from H, F, methyl optionally substituted with a fluorine (F), and $OCH_3$ optionally substituted with a F, $R_6$ is selected from $C_{1-6}$ alkyl, branched $C_{3-6}$ alkyl and $C_{3-7}$ cycloalkyl; or a pharmaceutically acceptable salt or solvate thereof.

In one embodiment the compound 3,3'-Dideoxy-3,3'-bis-[4-(2-thiophenyl]-1,1'-sulfanediyl-di-β-D-galactopyranoside is disclaimed.

In an embodiment A is selected from formula 2 and B is selected from formula 3.

In a further embodiment A is selected from formula 2 and Het1 is selected from a five membered hetero aromatic ring containing 1-4 nitrogen atoms, optionally 1 oxygen atom and optionally one sulphur atom.

In a still further embodiment A is selected from formula 2 and Het1 is selected from a six membered hetero aromatic ring containing 1-4 nitrogen atoms.

In a further embodiment A is selected from formula 2 and Het1 is selected from a pyridinyl, pyrimidinyl and imidazolyl.

In a still further embodiment B is selected from formula 3 and Het2 is selected from a five membered heteroaromatic ring, optionally substituted with a group selected from Br, F, Cl, methyl optionally substituted with a F (e.g. $CF_3$), and $OCH_3$ optionally substituted with a F (e.g. $OCF_3$).

In a further embodiment B is selected from formula 3 and Het2 is selected from a six membered heteroaromatic ring, optionally substituted with a group selected from Br, F, Cl, methyl optionally substituted with a F (e.g. $CF_3$), and $OCH_3$ optionally substituted with a F (e.g. $OCF_3$).

In a further embodiment B is selected from formula 3 and Het2 is selected from a six membered heteroaromatic ring, optionally substituted with a group selected from $NH_2$ and $NHC(=O)CH_3$.

In a still further embodiment A is selected from formula 2 and Het1 is selected from a five membered heteroaromatic ring, optionally substituted with a group selected from Br, F, Cl, methyl optionally substituted with a F (e.g. $CF_3$), and $OCH_3$ optionally substituted with a F (e.g. $OCF_3$).

In a further embodiment A is selected from formula 2 and Het1 is selected from a six membered heteroaromatic ring, optionally substituted with a group selected from Br, F, Cl, methyl optionally substituted with a F (e.g. $CF_3$), and $OCH_3$ optionally substituted with a F (e.g. $OCF_3$).

In a further embodiment A is selected from formula 2 and Het1 is selected from a six membered heteroaromatic ring, optionally substituted with a group selected from $NH_2$ and $NHC(=O)CH_3$.

In a still further embodiment B is selected from formula 3 and Het2 is selected from a five membered hetero aromatic ring containing 1-4 nitrogen atoms, optionally 1 oxygen atom and optionally one sulphur atom.

In a further embodiment B is selected from formula 3 and Het2 is selected from a six membered hetero aromatic ring containing 1-4 nitrogen atoms.

In a still further embodiment B is selected from formula 3 and Het2 is selected from a pyridinyl, pyrimidinyl, pyrazinyl, pyridazyl, oxazoyl, thiazoyl, thiadiazoyl, oxadiazoyl, thiophenyl and imidazolyl.

In a further embodiment A is selected from formula 2 and Het1 is selected from a five membered hetero aromatic ring containing 1-4 nitrogen atoms, optionally 1 oxygen atom and optionally one sulphur atom.

In a still further embodiment A is selected from formula 2 and Het1 is selected from a six membered hetero aromatic ring containing 1-4 nitrogen atoms.

In a further embodiment A is selected from formula 2 and Het1 is selected from a pyridinyl, pyrimidinyl, pyrazinyl, pyridazyl, oxazoyl, thiazoyl, thiadiazoyl, oxadiazoyl, thiophenyl and imidazolyl.

In a still further embodiment B is selected from formula 3 and Het2 is selected from a pyridinyl, pyrimidinyl, pyrazinyl, pyridazyl, oxazoyl, thiazoyl, thiadiazoyl, oxadiazoyl, thiophenyl and imidazolyl.

In a further embodiment A is selected from formula 2 and Het1 is selected from a five membered hetero aromatic ring containing 1-4 nitrogen atoms, optionally 1 oxygen atom and optionally one sulphur atom, substituted with a group selected from Br, F, Cl, $CF_3$, and $OCH_3$.

In a still further embodiment A is selected from formula 2 and Het1 is selected from a six membered hetero aromatic ring containing 1-4 nitrogen atoms, substituted with a group selected from Br, F, Cl, $CF_3$, Oxo and $OCH_3$.

In a further embodiment A is selected from formula 2 and Het1 is selected from a pyridinyl, pyrimidinyl, pyrazinyl, pyridazyl, oxazoyl, thiazoyl, thiadiazoyl, oxadiazoyl, thiophenyl, and imidazolyl, substituted with a group selected from Br, F, Cl, $CF_3$, and $OCH_3$; or pyridonyl.

In a further embodiment A is selected from formula 2 and Het1 is selected from a pyridinyl, pyrimidinyl, pyrazinyl, pyridazyl, oxazoyl, thiazoyl, thiadiazoyl, oxadiazoyl, thiophenyl, and imidazolyl substituted with a group selected from $NH_2$ and $NHC(\!=\!O)CH_3$. Such as pyridinyl substituted with a group selected from $NH_2$ and $NHC(\!=\!O)CH_3$.

In a still further embodiment B is selected from formula 3 and Het2 is selected from a five membered heteroaromatic ring, optionally substituted with a group selected from F, Cl, methyl optionally substituted with a F (e.g. $CF_3$), and $OCH_3$ optionally substituted with a F (e.g. $OCF_3$).

In a further embodiment B is selected from formula 3 and Het2 is selected from a six membered heteroaromatic ring, optionally substituted with a group selected from F, Cl, methyl optionally substituted with a F (e.g. $CF_3$), Oxo, and $OCH_3$ optionally substituted with a F (e.g. $OCF_3$).

In a further embodiment B is selected from formula 3 and Het2 is selected from a six membered heteroaromatic ring, optionally substituted with a group selected from $NH_2$, and $NHC(\!=\!O)CH_3$.

In a still further embodiment A is selected from formula 2 and Het1 is selected from a five membered heteroaromatic ring, optionally substituted with a group selected from F, Cl, methyl optionally substituted with a F (e.g. $CF_3$), and $OCH_3$ optionally substituted with a F (e.g. $OCF_3$).

In a further embodiment A is selected from formula 2 and Het1 is selected from a six membered heteroaromatic ring, optionally substituted with a group selected from F, Cl, methyl optionally substituted with a F (e.g. $CF_3$), Oxo, and $OCH_3$ optionally substituted with a F (e.g. $OCF_3$).

In a still further embodiment B is selected from formula 3 and Het2 is selected from a five membered hetero aromatic ring containing 1-4 nitrogen atoms, optionally 1 oxygen atom and optionally one sulphur atom, substituted with a group selected from Br, F, Cl, $CF_3$, and $OCH_3$.

In a further embodiment B is selected from formula 3 and Het2 is selected from a six membered hetero aromatic ring containing 1-4 nitrogen atoms, substituted with a group selected from Br, F, Cl, $CF_3$, Oxo, and $OCH_3$.

In a further embodiment B is selected from formula 3 and Het2 is selected from a six membered hetero aromatic ring containing 1-4 nitrogen atoms, substituted with a group selected from $NH_2$ and $NHC(\!=\!O)CH_3$.

In a still further embodiment B is selected from formula 3 and Het2 is selected from a pyridinyl, pyrimidinyl, pyrazinyl, pyridazyl, oxazoyl, thiazoyl, thiadiazoyl, oxadiazoyl, thiophenyl, and imidazolyl, substituted with a group selected from Br, F, Cl, $CF_3$, and $OCH_3$; or pyridonyl.

In a further embodiment A is selected from formula 2 and Het1 is selected from a five membered hetero aromatic ring containing 1-4 nitrogen atoms, optionally 1 oxygen atom and optionally one sulphur atom, substituted with a group selected from Br, F, Cl, $CF_3$, and $OCH_3$.

In a still further embodiment A is selected from formula 2 and Het1 is selected from a six membered hetero aromatic ring containing 1-4 nitrogen atoms, substituted with a group selected from Br, F, Cl, $CF_3$, Oxo, and $OCH_3$.

In a further embodiment A is selected from formula 2 and Het1 is selected from a pyridinyl, pyrimidinyl, pyrazinyl, pyridazyl, thiazoyl, thiadiazoyl, oxadiazoyl, thiophenyl, and imidazolyl, substituted with a group selected from Br, F, Cl, $CF_3$, and $OCH_3$; or pyridonyl.

In a still further embodiment B is selected from formula 3 and Het2 is selected from a five membered hetero aromatic ring containing 1-4 nitrogen atoms, optionally 1 oxygen atom and optionally one sulphur atom, substituted with a group selected from Br, F, Cl, $CF_3$, and $OCH_3$.

In a still further embodiment B is selected from formula 3 and Het2 is selected from a pyridinyl, pyrimidinyl, pyrazinyl, pyridazyl, oxazoyl, thiazoyl, thiadiazoyl, oxadiazoyl, thiophenyl, and imidazolyl, substituted with a group selected from Br, F, Cl, $CF_3$, and $OCH_3$; or pyridonyl.

In a further embodiment A is selected from formula 2 and B is selected from formula 4.

In a still further embodiment A is selected from formula 2 and Het1 is selected from a five membered hetero aromatic ring containing 1-4 nitrogen atoms, optionally 1 oxygen atom and optionally one sulphur atom, optionally substituted with a group selected from Br, F, Cl, $CF_3$, and $OCH_3$; and B is selected from formula 4 and $R_1$-$R_5$ are independently selected from H, F, methyl optionally substituted with a fluorine (F), and $OCH_3$ optionally substituted with a F.

In a further embodiment A is selected from formula 2 and Het1 is selected from a six membered hetero aromatic ring containing 1-4 nitrogen atoms, optionally substituted with a group selected from Br, F, Cl, $CF_3$, Oxo, and $OCH_3$; and B is selected from formula 4 and $R_1$-$R_5$ are independently selected from H, F, methyl optionally substituted with a fluorine (F), and $OCH_3$ optionally substituted with a F.

In a still further embodiment A is selected from formula 2 and Het1 is selected from a pyridinyl, pyrimidinyl, pyrazinyl, pyridazyl, oxazoyl, thiazoyl, thiadiazoly, oxadiazoyl, thiophenyl, and imidazolyl, substituted with a group selected from Br, F, Cl, $CF_3$, and $OCH_3$; or pyridonyl; and B is selected from formula 4 and $R_1$-$R_5$ are independently selected from H, F, methyl optionally substituted with a fluorine (F), and $OCH_3$ optionally substituted with a F.

In a further embodiment B is selected from formula 4 and $R_1$-$R_5$ are independently selected from H and F, provided that at least one of $R_2$-$R_4$ is selected from a F. In a further embodiment $R_1$ and $R_5$ are H, and $R_2$-$R_4$ are F.

In a further embodiment A is selected from formula 2 and B is selected from formula 5.

In a still further embodiment A is selected from formula 2 and Het1 is selected from a five membered hetero aromatic ring containing 1-4 nitrogen atoms, optionally 1 oxygen atom and optionally one sulphur atom, optionally substituted with a group selected from Br, F, Cl, $CF_3$, and $OCH_3$; and B is selected from formula 5 and $R_6$ is selected from $C_{1-6}$ alkyl, branched $C_{3-6}$ alkyl and $C_{3-7}$ cycloalkyl.

In a further embodiment A is selected from formula 2 and Het1 is selected from a six membered hetero aromatic ring containing 1-4 nitrogen atoms, optionally substituted with a group selected from Br, F, Cl, $CF_3$, Oxo, and $OCH_3$; and B is selected from formula 5 and $R_6$ is selected from $C_{1-6}$ alkyl, branched $C_{3-6}$ alkyl and $C_{3-7}$ cycloalkyl.

In a still further embodiment A is selected from formula 2 and Het1 is selected from a pyridinyl, pyrimidinyl, pyrazinyl, pyridazyl, oxazoyl, thiazoyl, thiadiazoyl, oxadiazoyl, thiophenyl, and imidazolyl, substituted with a group selected from Br, F, Cl, $CF_3$, and $OCH_3$; or pyridonyl; and B is selected from formula 5 and $R_6$ is selected from $C_{1-6}$ alkyl, branched $C_{3-6}$ alkyl and $C_{3-7}$ cycloalkyl.

In a further embodiment the compound of formula (1) is selected from 3,3'-Dideoxy-3,3'-bis-[4-(5-fluoropyridin-2-yl)-1H-1,2,3-triazol-1-yl]-1,1'-sulfanediyl-di-β-D-galactopyranoside, 3,3'-Dideoxy-3,3'-bis-[4-(6-methoxypyridin-3-yl)-1H-1,2,3-triazol-1-yl]-1,1'-sulfanediyl-di-β-D-galactopyranoside, 3,3'-Dideoxy-3,3'-bis-[4-(1-methyl-1H-imidazol-5-yl)-1H-1,2,3-triazol-1-yl]-1,1'-sulfanediyl-di-β-D-galactopyranoside, 3,3'-Dideoxy-3,3'-bis-[4-(3-chloro-5-trifluoromethyl-pyridin-2-yl)-1H-1,2,3-triazol-1-yl]-1,1'-sulfanediyl-di-β-D-galactopyranoside, 3,3'-Dideoxy-3,3'-bis-[4-(pyrimidin-5-yl)-1H-1,2,3-triazol-1-yl]-1,1'-sulfanediyl-di-β-D-galactopyranoside, 3,3'-Dideoxy-3,3'-bis-[4-(pyridin-2-yl)-1H-1,2,3-triazol-1-yl]-1,1'-sulfanediyl-di-β-D-galactopyranoside, and 3,3'-Dideoxy-3-[4-(5-fluoropyridin-2-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside.

In a still further embodiment the compound of formula (1) is selected from 3,3'-Dideoxy-3-[4-(pyridin-3-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside, 3,3'-Dideoxy-3-[4-(1,3-pyrimidin-5-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside, 3,3'-Dideoxy-3-[4-(1,3-pyrimidin-2-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside, 3,3'-Dideoxy-3-[4-(pyridin-2-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside, 3,3'-Dideoxy-3-[4-(pyridin-4-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside, 3-[4-((2-acetamid-N-yl)-pyridin-5-yl)-3,3'-dideoxy-1H-1,2,3-triazol-1-yl]-3'-[4-(3,4,5-trifluorophenyl)-1H-1,2,3-triazol-1-yl]-1,1'-sulfanediyl-di-β-D-galactopyranoside, 3-[4-(2-aminopyridin-5-yl)-3,3'-dideoxy-1H-1,2,3-triazol-1-yl]-3'-[4-(3,4,5-trifluorophenyl)-1H-1,2,3-triazol-1-yl]-1,1'-sulfanediyl-di-β-D-galactopyranoside, and 3,3'-Dideoxy-3-[4-(5-fluoro-1,3-pyrimidin-2-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside.

In a further aspect the present invention relates to a compound of formula 1 of the present invention for use as a medicine.

In a still further aspect the present invention relates to a pharmaceutical composition comprising a compound of formula 1 of the present invention and optionally a pharmaceutically acceptable additive, such as carrier or excipient.

In a further aspect the present invention relates to a compound of formula 1 of the present invention for use in a method for treating a disorder relating to the binding of a galectin, such as galectin-1 and galectin-3 to a ligand in a mammal, such as a human.

In a further embodiment the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; asthma and other interstitial lung diseases, including Hermansky-Pudlak syndrome, mesothelioma; liver disorders, such as non-alcoholic steatohepatitis.

In a still further aspect the present invention relates to a method for treatment of a disorder relating to the binding of a galectin, such as galectin-1 and galectin-3, to a ligand in a mammal, such as a human, wherein a therapeutically effective amount of at least one compound of formula (1) of the present invention is administered to a mammal in need of said treatment.

In a further embodiment of the present invention, the disorder is selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; asthma and other intestinal lung diseases, including Hermansky-Pudlak syndrome, mesothelioma; liver disorders, such as non-alcoholic steatohepatitis.

Another aspect of the present invention concerns combination therapy involving administering a compound of formula (1) and the present invention together with a therapeutically active compound different from the compound of formula (1) (interchangeable with a "a different therapeutically active compound"). In one embodiment the present invention relates to a combination of a compound of formula (1) and a different therapeutically active compound for use in treatment of a disorder relating to the binding of a galectin, such as galectin-1 and galectin-3, to a ligand in a mammal. Such disorders are disclosed below.

In an embodiment of the present invention, a therapeutically effective amount of at least one compound of formula (1) of the present invention is administered to a mammal in need thereof in combination with a different therapeutically active compound. In a further embodiment, said combination of a compound of formula (1), in combination with a different therapeutically active compound is administered to a mammal suffering from a disorder selected from the group consisting of inflammation; fibrosis, such as pulmonary fibrosis, liver fibrosis, kidney fibrosis, ophthalmological fibrosis and fibrosis of the skin and heart; scarring; keloid formation; aberrant scar formation; surgical adhesions; septic shock; cancer, such as carcinomas, sarcomas, leukemias and lymphomas, such as T-cell lymphomas; metastasising cancers; autoimmune diseases, such as psoriasis, rheumatoid arthritis, Crohn's disease, ulcerative colitis, ankylosing spondylitis, systemic lupus erythematosus; metabolic disorders; heart disease; heart failure; pathological angiogenesis, such as ocular angiogenesis or a disease or condition associated with ocular angiogenesis, e.g. neovascularization related to cancer; and eye diseases, such as age-related macular degeneration and corneal neovascularization; atherosclerosis; metabolic diseases such as diabetes; asthma and other intestinal lung diseases, including Hermansky-Pudlak syndrome, mesothelioma; liver disorders, such as non-alcoholic steatohepatitis.

A non-limiting group of cancers given as examples of cancers that may be treated, managed and/or prevented by administration of a compound of formula (1) in combination with a different therapeutically active compound is selected from: colon carcinoma, breast cancer, pancreatic cancer, ovarian cancer, prostate cancer, fibrosarcoma, myxosarcoma, liposarcoma, chondrosarcoma, osteogenic sarcoma, chordoma, angiosarcoma, endotheliosarcoma, lymphangeosarcoma, lymphangeoendothelia sarcoma, synovioma, mesothelioma, Ewing's sarcoma, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystandeocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioblastomas, neuronomas, craniopharingiomas, schwannomas, glioma, astrocytoma, medulloblastoma, craniopharyngioma, ependymoma, pinealoma, hemangioblastoma, acoustic neuroama, oligodendroglioma, meningioma, melanoma, neuroblastoma, retinoblastoma, leukemias and lymphomas, acute lymphocytic leukemia and acute myelocytic polycythemia vera, multiple myeloma, Waldenstrom's macroglobulinemia, and heavy chain disease, acute nonlymphocytic leukemias, chronic lymphocytic leukemia, chronic myelogenous leukemia, Hodgkin's Disease, non-Hodgkin's lymphomas, rectum cancer, urinary cancers, uterine cancers, oral cancers, skin cancers, stomach cancer, brain tumors, liver cancer, laryngeal cancer, esophageal cancer, mammary tumors, childhood-null acute lymphoid leukemia (ALL), thymic ALL, B-cell ALL, acute myeloid leukemia, myelomonocytoid leukemia, acute megakaryocytoid leukemia, Burkitt's lymphoma, acute myeloid leukemia, chronic myeloid leukemia, and T cell leukemia, small and large non-small cell lung carcinoma, acute granulocytic leukemia, germ cell tumors, endometrial cancer, gastric cancer, cancer of the head and neck, chronic lymphoid leukemia, hair cell leukemia and thyroid cancer.

In some aspects of the present invention, the administration of at least one compound of formula (1) of the present invention and at least one additional therapeutic agent demonstrate therapeutic synergy. In some aspects of the methods of the present invention, a measurement of response to treatment observed after administering both at least one compound of formula (1) of the present invention and the additional therapeutic agent is improved over the same measurement of response to treatment observed after administering either the at least one compound of formula (1) of the present invention or the additional therapeutic agent alone.

A further aspect of the present invention concerns combination therapy involving administering a compound of formula (1) of the present invention together with an anti-fibrotic compound different form the compound of formula (1) to a mammal in need thereof. In a further embodiment, such anti-fibrotic compound may be selected from the following non-limiting group of anti-fibrotic compounds: pirfenidone, nintedanib, simtuzumab (GS-6624, AB0024), BG00011 (STX100), PRM-151, PRM-167, PEG-FGF21, BMS-986020, FG-3019, MN-001, IW001, SAR156597, GSK2126458, and PBI-4050.

A still further aspect of the present invention concerns combination therapy involving administering a compound of formula (1) in combination with a further conventional cancer treatment such as chemotherapy or radiotherapy, or treatment with immunostimulating substances, gene therapy, treatment with antibodies and treatment using dendritic cells, to a mammal in need thereof.

In an embodiment the compound of formula (1) is administered together with at least one additional therapeutic agent selected from an antineoplastic chemotherapy agent. In a further embodiment, the antineoplastic chemotherapeutic agent is selected from: all-trans retinoic acid, Actimide, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Etoposide, Fludarabine, Fluorouracil, Gemcitabine, Hydroxyurea, Idarubicin, Irinotecan, Lenalidomide, Leucovorin, Mechlorethamine, Melphalan, Mercaptopurine, Methotrexate, Mitoxantrone, Oxaliplatin, Paclitaxel, Pemetrexed, Revlimid, Temozolomide, Teniposide, Thioguanine, Valrubicin, Vinblastine, Vincristine, Vindesine and Vinorelbine. In one embodiment, a chemotherapeutic agent for use in the combination of the present agent may, itself, be a combination of different chemotherapeutic agents. Suitable combinations include FOLFOX and IFL. FOLFOX is a combination which includes 5-fluorouracil (5-FU), leucovorin, and oxaliplatin. IFL treatment includes irinotecan, 5-FU, and leucovorin.

In a further embodiment of the present invention, the further conventional cancer treatment includes radiation therapy. In some embodiments, radiation therapy includes localized radiation therapy delivered to the tumor. In some embodiments, radiation therapy includes total body irradiation.

In other embodiments of the present invention the further cancer treatment is selected from the group of immunostimulating substances e.g. cytokines and antibodies. Such as cytokines may be selected from the group consisting of, but not limited to: GM-CSF, type I IFN, interleukin 21, interleukin 2, interleukin 12 and interleukin 15. The antibody is preferably an immunostimulating antibody such as anti-CD40 or anti-CTLA-4 antibodies. The immunostimulatory substance may also be a substance capable of depletion of immune inhibitory cells (e.g. regulatory T-cells) or factors, said substance may for example be E3 ubiquitin ligases. E3 ubiquitin ligases (the HECT, RING and U-box proteins) have emerged as key molecular regulators of immune cell function, and each may be involved in the regulation of immune responses during infection by targeting specific inhibitory molecules for proteolytic destruction. Several HECT and RING E3 proteins have now also been linked to the induction and maintenance of immune self-tolerance:

c-Cbl, Cbl-b, GRAIL, Itch and Nedd4 each negatively regulate T cell growth factor production and proliferation.

In some embodiments of the present invention the compound of formula (1) is administered together with at least one additional therapeutic agent selected from a checkpoint inhibitor. In some embodiments of the invention, the checkpoint inhibitor is acting on one or more of the following, non-limiting group of targets: CEACAM1, galectin-9, TIM3, CD80, CTLA4, PD-1, PD-L1, HVEM, BTLA, CD160, VISTA, B7-H4, B7-2, CD155, CD226, TIGIT, CD96, LAG3, GITF, OX40, CD137, CD40, IDO, and TDO. These are know targets and some of these targets are described in Melero et al., Nature Reviews Cancer (2015).

In some embodiments of the present invention the compound of formula (1) is administered together with at least one additional therapeutic agent selected from an inhibitor of indoleamine-2,3-dioxygenase (IDO).

In some embodiments of the present invention the compound of formula (1) is administered together with at least one additional therapeutic agent selected from one or more inhibitors of the CTLA4 pathway. In some embodiments, the inhibitor of the CTLA4 pathway is selected from one or more antibodies against CTLA4.

In some embodiments of the present invention the compound of formula (1) is administered together with at least one additional therapeutic agent selected from one or more inhibitors of the PD-1/PD-L pathway. In some embodiments, the one or more inhibitors of the PD-1/PD-L pathway are selected from one or more antibodies against PD-1, PD-L1, and/or PD-L2.

The skilled person will understand that it may be necessary to adjust or change the order of steps in the process a1 to a11, and such change of order is encompassed by the aspects of the process as described above in the reaction schemes and accompanying description of the process steps.

Furthermore the skilled person will understand that the processes described above and hereinafter the functional groups of intermediate compounds may need to be protected by protecting group.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkyl silyl or diarylalkylsilyl groups (e.g., t-butyldimethylsilyl, t-butyldipheylsilyl or trimethylsilyl), AcO (acetoxy), TBS(t-butyldimethylsilyl), TMS (trimethylsilyl), PMB (p-methoxybensyl), and tetrahydropyranyl. Suitable protecting groups for carboxylic acid include (C1-C6)-alkyl or benzyl esters. Suitable protecting groups for amino include t-butyloxycarbonyl, benzyloxycarbonyl, 2-(trimethylsilyl)-ethoxy-methyl or 2-trimethylsilylethoxycarbonyl (Teoc). Suitable protecting groups for S include S—C(=N)NH$_2$, TIPS.

The protection and deprotection of functional groups may take place before or after any reaction in the above mentioned processes.

Furthermore the skilled person will appreciate that, in order to obtain compounds of the invention in an alternative, and on some occasions, more convenient, manner, the individual process steps mentioned hereinbefore may be performed in different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

In a still further embodiment the compound 1 is on free form. In one embodiment the free form is an anhydrate. In another embodiment the free form is a solvate, such as a hydrate.

In a further embodiment the compound is a crystalline form. The skilled person may carry out tests in order to find polymorphs, and such polymorphs are intended to be encompassed by the term "crystalline form" as used herein.

When the compounds and pharmaceutical compositions herein disclosed are used for the above treatment, a therapeutically effective amount of at least one compound is administered to a mammal in need of said treatment.

The term "$C_{1-x}$ alkyl" as used herein means an alkyl group containing 1-x carbon atoms, e.g. $C_{1-5}$ or $C_{1-6}$, such as methyl, ethyl, propyl, butyl, pentyl or hexyl.

The term "branched $C_{3-6}$ alkyl" as used herein means a branched alkyl group containing 3-6 carbon atoms, such as isopropyl, isobutyl, tert-butyl, isopentyl, 3-methylbutyl, 2,2-dimethylpropyl, n-hexyl, 2-methylpentyl, 2,2-dimethylbutyl, 2,3-dimethylbutyl.

The term "$C_{3-7}$ cycloalkyl" as used herein means a cyclic alkyl group containing 3-7 carbon atoms, such as cyclopropyl, cyclobutyl, cyclopentyl, cyclohexyl, cycloheptyl, and 1-methylcyclopropyl.

The term "C(=O)" as used herein means a carbonyl group.

The term "Oxo" as used herein means an oxygen atom with double bonds, also indicated as =O.

The term "a five or six membered heteroaromatic ring" as used herein means one five membered heteroaromatic ring or one six membered heteroaromatic ring. The five membered heteroaromatic ring contains 5 ring atoms of which one to four are heteroatoms selected from N, O, and S. The six membered heteroaromatic ring contains 6 ring atoms of which one to five are heteroatoms selected from N, O and S. Examples include thiophene, furan, pyran, pyrrole, imidazole, pyrazole, isothiazole, isooxazole, pyridine, pyrazine, pyrimidine and pyridazine. When such heteroaromatic rings are substituents they are termed thiophenyl, furanyl, pyranyl, pyrrolyl, imidazolyl, pyrazolyl, isothiazolyl, isooxazolyl, pyridinyl, pyrazinyl, pyrimidinyl and pyridazinyl. Also included are oxazoyl, thiazoyl, thiadiazoly, oxadiazoyl, and pyridonyl.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular a human being, but it may also include animals, such as dogs, cats, cows, sheep and pigs.

The term "a therapeutically effective amount" of a compound of formula (1) of the present invention as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the present invention relates to a pharmaceutical composition comprising the compound of formula (1) and optionally a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (1) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99 weight % of said at least one pharmaceutically acceptable adjuvant, diluent, excipient and/or carrier and from 1 to 99 weight % of a compound as herein disclosed. The combined amount of the active ingredient and of the pharmaceutically acceptable adjuvant, diluent, excipient and/or carrier may not constitute more than 100% by weight of the composition, particularly the pharmaceutical composition.

In some embodiments, only one compound as herein disclosed is used for the purposes discussed above.

In some embodiments, two or more of the compound as herein disclosed are used in combination for the purposes discussed above.

The composition, particularly pharmaceutical composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

Experimental Procedures

Evaluation of Kd Values

The affinity of compounds S4a-f for galectins were determined by a fluorescence anisotropy assay where the compound was used as in inhibitor of the interaction between galectin and a fluorescein tagged saccharide probe as described Sörme, P., Kahl-Knutsson, B. Huflejt, M., Nilsson, U. J., and Leffler H. (2004) Fluorescence polarization as an analytical tool to evaluate galectin-ligand interactions. Anal. Biochem. 334: 36-47, (Sörme et al., 2004) and Monovalent interactions of Galectin-1 By Salomonsson, Emma; Larumbe, Amaia; Tejler, Johan; Tullberg, Erik; Rydberg, Hanna; Sundin, Anders; Khabut, Areej; Frejd, Torbjorn; Lobsanov, Yuri D.; Rini, James M.; et al, From Biochemistry (2010), 49(44), 9518-9532, (Salomonsson et al., 2010). The assay was adapted to be able to measure the high affinity of the present compound for galectin-3 by using the below probe constructed to have high affinity for galectin-3 based on the structure of Ref 1 which made it possible to use a low concentration of galectin-3 (50 nM). 100 nM albumin was included as a carrier to prevent protein loss at such low concentration of galectin.

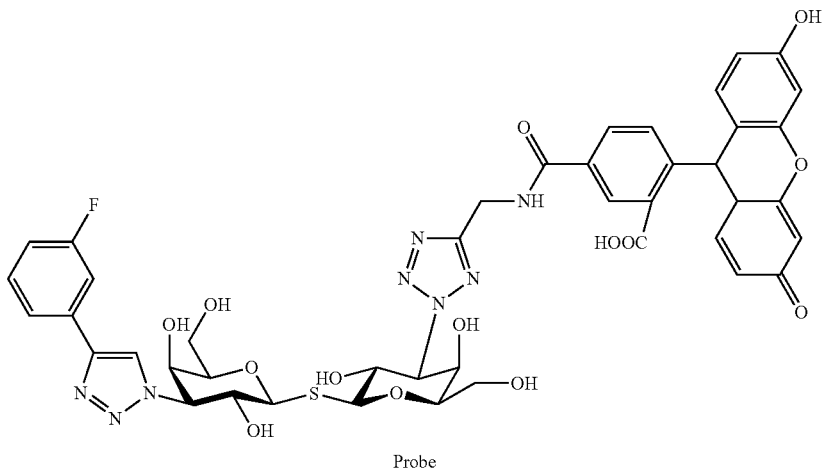

Probe

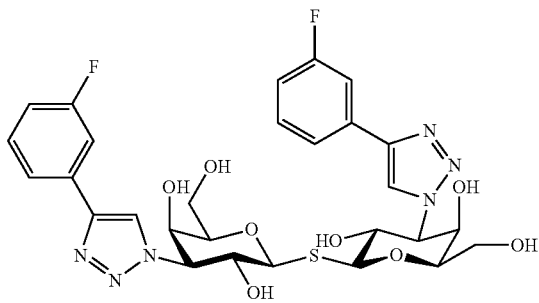

Ref 1. 3,3'-bis-[4-(3-fluorophenyl)-1H-1,2,3-triazol-1-yl]-1,1'-sulfanediyl-di-β-D-galactopyranoside Kd values for compounds s4a-f, S7, S8a-h and reference compound ref 1

| Example | Compound Structure | Galectin-3 Kd (µM) | Galectin 1 Kd (µM) | Solubility buffer* (mg/ml) | Solubility water (mg/ml) |
|---|---|---|---|---|---|
| S4a | 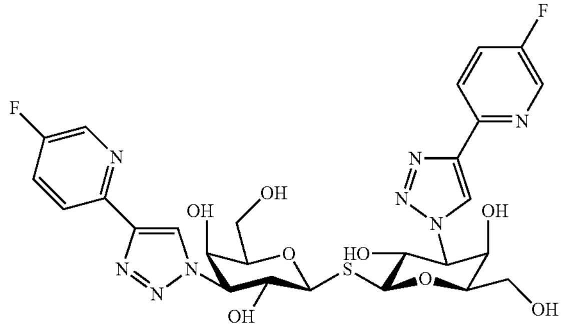 | 0.010 | 0.021 | 2.6 | 4.3 |

| Example | Compound Structure | Galectin-3 Kd (μM) | Galectin 1 Kd (μM) | Solubility buffer* (mg/ml) | Solubility water (mg/ml) |
|---|---|---|---|---|---|
| S4b | 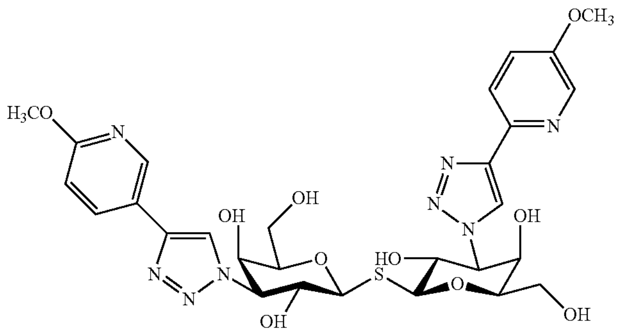 | 0.012 | 0.12 | | |
| S4c | 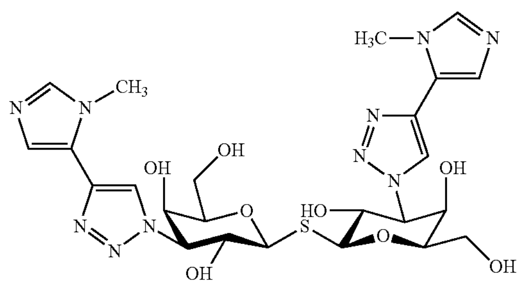 | 0.131 | 0.60 | | |
| S4d | 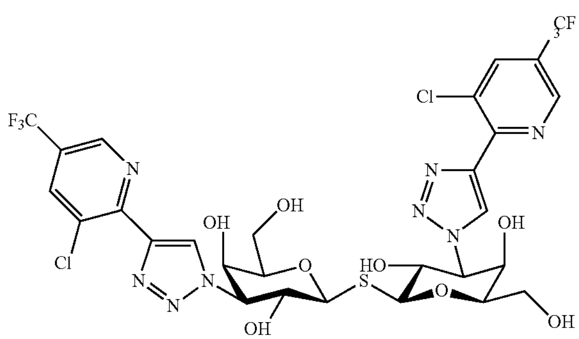 | 0.025 | 0.74 | 0.2 | |
| S4e | 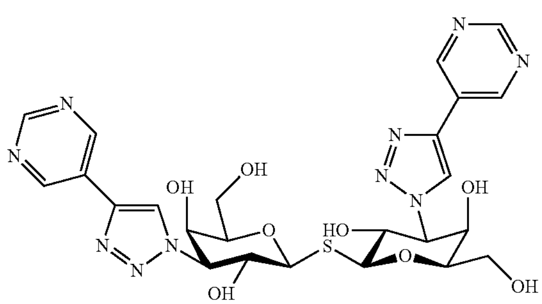 | 0.044 | 0.39 | 0.007 | |
| S4f | 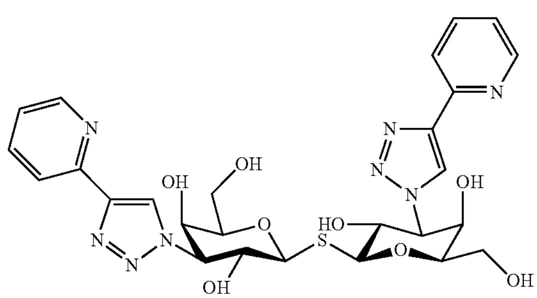 | 0.042 | 0.21 | 0.45 | |

-continued

| Example | Compound Structure | Galectin-3 Kd (μM) | Galectin 1 Kd (μM) | Solubility buffer* (mg/ml) | Solubility water (mg/ml) |
|---|---|---|---|---|---|
| S7 | 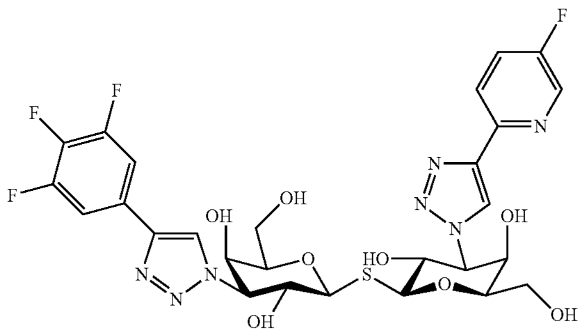 | <0.005 | 0.04 | | |
| S8a | 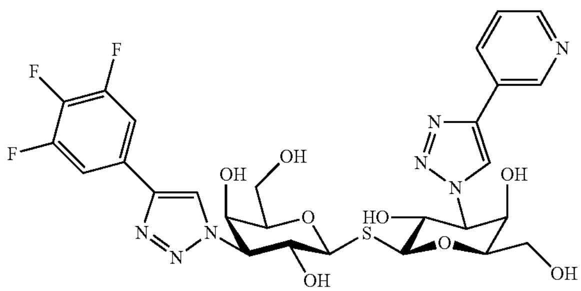 | 0.002 | 0.038 | 0.041 | |
| S8b | 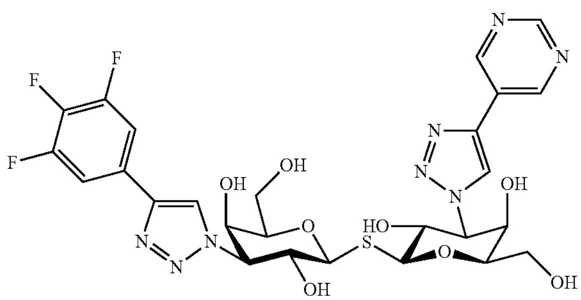 | <0.002 | 0.080 | 0.36 | |
| S8c | 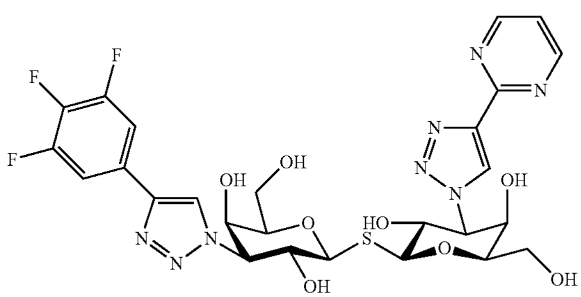 | <0.002 | 0.070 | 4.6 | |
| S8d | 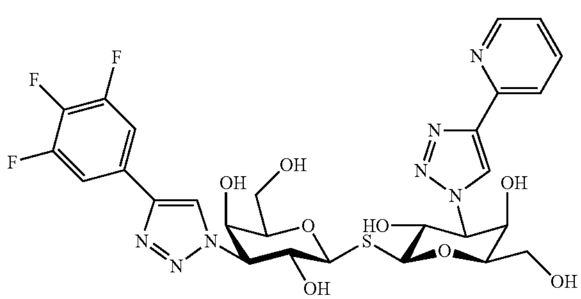 | 0.001 | 0.038 | 1.4 | |

-continued

| Example | Compound Structure | Galectin-3 Kd (μM) | Galectin 1 Kd (μM) | Solubility buffer* (mg/ml) | Solubility water (mg/ml) |
|---|---|---|---|---|---|
| S8e | 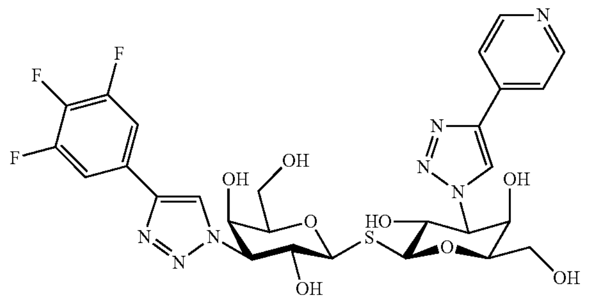 | 0.001 | 0.072 | 1.3 | |
| S8f | 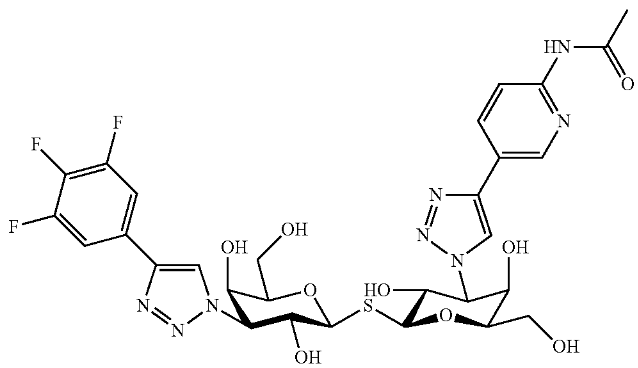 | 0.005 | 0.149 | 0.77 | |
| S8g | 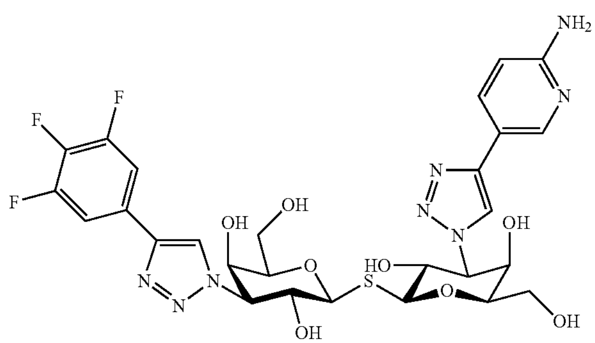 | <0.002 | 0.034 | 1.8 | |
| S8h | 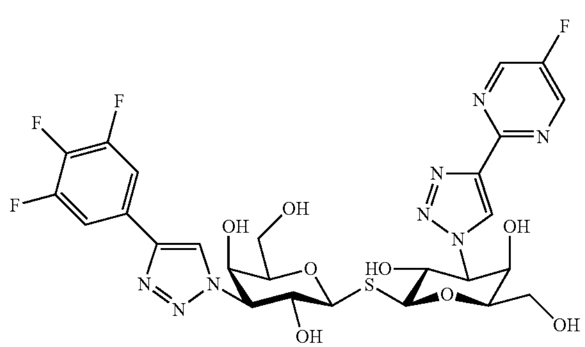 | <0.002 | 0.055 | 3.3 | |

| Example | Compound Structure | Galectin-3 Kd (µM) | Galectin 1 Kd (µM) | Solubility buffer* (mg/ml) | Solubility water (mg/ml) |
|---|---|---|---|---|---|
| Ref 1 | 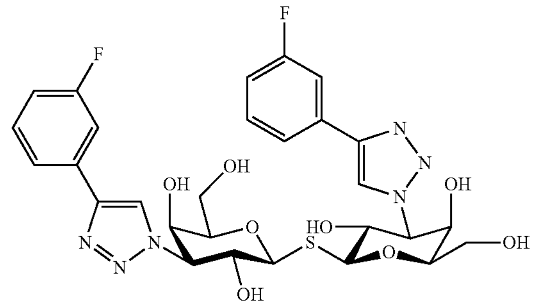 | 0.002 | 0.040 | | 0.4 |

*0.1 M phosphate buffer pH 6.5

Synthesis

Materials and Methods

Commercial reagents were used without further purification unless otherwise stated.

Analytical TLC was performed on silica gel 60-$F_{254}$ (Merck) with detection by fluorescence and by immersion in a 10% ethanolic solution of sulfuric acid. Followed by charring.

Nuclear Magnetic Resonance (NMR) spectra were recorded on a Bruker DRX 400 MHz spectrometer, 400 MHz Varian or a 500 MHz Bruker AVANCE III 500 instrument, at 25° C. Chemical shifts are reported in ppm (δ) using the residual solvent as internal standard. Peak multiplicities are expressed as follow: s, singlet; d, doublet; dd, doublet of doublets; t, triplet; dt, double of triplet; q, quartet; m, multiplet; br s, broad singlet.

LC-MS were acquired on an Agilent 1100 or Agilent 1200 HPLC coupled with an Agilent MSD mass spectrometer operating in ES (+) ionization mode. Columns: Waters symmetry 2.1×30 mm C18, Chromolith RP-18 2×50 mm or XBridge C18 (4.6×50 mm, 3.5 µm) or Sun-Fire C18 (4.6×50 mm, 3.5 µm). Solvent A water+0.1% TFA and solvent B Acetonitrile+0.1% TFA. Wavelength: 254 nM. ESI-MS was recorded on a Micromass Q-TOF mass spectrometer.

Preparative HPLC was performed on a Gilson system. A) Flow: 10 ml/min Column: kromasil 100-5-C18 column. Wavelength: 254 nM. Solvent A water+0.1% TFA and solvent B Acetonitrile+0.1% TFA. B) on a Gilson 215, Flow: 25 ml/min Column: XBrige prep C18 10 µm OBD (19×250 mm) column. Wavelength: 254 nM. Solvent A water (10 mM Ammonium hydrogen carbonate) and solvent B Acetonitrile.

Flash chromatography was performed on a Biotage Sp1 automated system, using Biotage Snap KP-Sil 25 g or 50 g cartridges or by column chromatography on silica gel (Amicon Matrex 35-70 µM, 60 Å).

General synthesis scheme for compounds S4a-f wherein $Y_1$ is defined as Het1 and Y2 is defined as He2 and $Het_1$=$Het_2$;

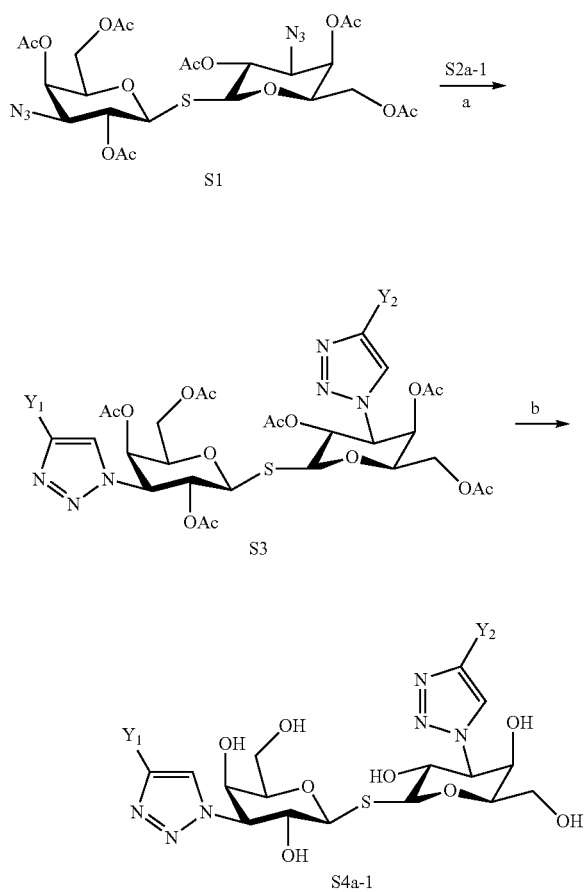

Copper-catalyzed multi-component reaction of acetylated 3-azido galactoside S1, S2a-f (a) CuI, $Et_3N$, dry DMF, rt, $N_2$ atm; (b) 0.5 M NaOMe in MeOH, rt Synthesis of Example s4a-f

| IUPAC name | Alkyne | Example | Yield (%) |
|---|---|---|---|
| 3,3'-Dideoxy-3,3'-bis-[4-(5-fluoropyridin-2-yl)-1H-1,2,3-triazol-1-yl]-1,1'-sulfanediyl-di-β-D-galactopyranoside | S2a | S4a | 85 |
| 3,3'-Dideoxy-3,3'-bis-[4-(6-methoxypyridin-3-yl)-1H-1,2,3-triazol-1-yl]-1,1'-sulfanediyl-di-β-D-galactopyranoside | S2b | S4b | 87 |
| 3,3'-Dideoxy-3,3'-bis-[4-(1-methyl-1H-imidazol-5-yl)-1H-1,2,3-triazol-1-yl]-1,1'-sulfanediyl-di-β-D-galactopyranoside | S2c | S4c | 94 |
| 3,3'-Dideoxy-3,3'-bis-[4-(3-chloro-5-trifluoromethyl-pyridin-2-yl)-1H-1,2,3-triazol-1-yl]-1,1'-sulfanediyl-di-β-D-galactopyranoside | S2d | S4d | 65 |

| IUPAC name | Alkyne | Example | Yield (%) |
|---|---|---|---|
| 3,3'-Dideoxy-3,3'-bis-[4-(pyrimidin-5-yl)-1H-1,2,3-triazol-1-yl]-1,1'-sulfanediyl-di-β-D-galactopyranoside | S2e | S4e | 86 |
| 3,3'-Dideoxy-3,3'-bis-[4-(pyridin-2-yl)-1H-1,2,3-triazol-1-yl]-1,1'-sulfanediyl-di-β-D-galactopyranoside | S2f | S4f | 85 |

S4a) 3,3'-Dideoxy-3,3'-bis-[4-(5-fluoro-2-pyridin-2-yl)-1H-1,2,3-triazol-1-yl]-1,1'-sulfanediyl-di-β-D-galactopyranoside a) A solution of carbohydrate azide S1 (156 mg, 0.226 mmol), Alkyne (S2a) (41 mg, 0.339 mmol), CuI (2 mg, 0.0113 mmol) in dry DMF (10 mL) in a 25 mL round bottomed flask was stirred under nitrogen for 1 hour. Et$_3$N (0.016 mL, 0.113 mmol) was then added slowly via syringe. The resulting solution was allowed to stir at room temperature for 12 hours when TLC showed complete conversion of the starting carbohydrate azide (1:2, n-heptane-EtOAc). Solvents were evaporated in vacuo and the residue was dissolved in CH$_2$Cl$_2$ (10 mL) and washed successively with aqueous NH$_4$Cl (2×10 mL) and brine (10 mL). The organic layer was separated, dried (Na$_2$SO$_4$) and evaporated in vacuo. The residue was purified by flash chromatography using n-hepatne-EtOAc as eluent to afford pure acetylated glycosylated triazole (3a) in 86% yield.

b) This was then deprotected using 0.5M NaOMe in MeOH and after the reaction was complete, it was neutralized using DOWEX H$^+$ resin. The resin was filtered and the crude was purified by flash chromatography using CH$_2$Cl$_2$:MeOH as eluent. This afforded the white solid compound S4a in 85% yield. White amorphous solid. $^1$H NMR (CD$_3$OD, 400 MHz) δ: 8.63 (s, 2H, triazole-H), 8.46 (d, 2H, 2.8 Hz, Ar—H), 8.10 (dd, 2H, 8.8 and 4.4 Hz, Ar—H), 7.71 (m, 2H, Ar—H), 4.95-4.92 (m, 4H, H1, H3), 4.70 (dd, 2H, 10.0 Hz, H2), 4.17 (d, 2H, 2.4 Hz, H4), 3.9-3.7 (6H, H5, H6). $^{13}$C NMR (CD$_3$OD, 100 MHz) δ: 161.73, 159.20, 147.92, 147.88, 138.76, 138.51, 125.49, 125.30, 123.76, 122.58, 86.50 (C-1), 81.40 (C-5), 69.72, 68.91, 68.45, 62.77 (C-6). HRMS m/z calcd for C$_{26}$H$_{29}$N$_8$O$_8$SF$_2$ (M+H$^+$), 651.1797; found, 651.1810.

Examples s4b-f were made using a similar procedure as compound s4a giving the yields described in the table above, and analytical data as described below;

S4b) 3,3'-Dideoxy-3,3'-bis-[4-(6-methoxypyridin-3-yl)-1H-1,2,3-triazol-1-yl]-1,1'-sulfanediyl-di-β-D-galactopyranoside White amorphous solid. $^1$H NMR (CD$_3$OD, 400 MHz) δ: 8.54 (s, 4H, triazole-H, ArH), 8.05 (d, 2H, 8.4 Hz, ArH), 6.84 (d, 2H, 8.4 Hz, ArH), 4.88 (6H obscured under H$_2$O, H-1, H-3, H-2), 4.19 (d, 2H, H-4), 3.91 (s, 6H, OCH$_3$), 3.89-3.71 (m, 6H, H-5, H-6). $^{13}$C NMR (CD$_3$OD, 100 MHz) δ: 165.41, 145.29, 144.82, 121.77, 121.59, 111.99, 86.85 (C-1), 81.42 (C-5), 69.77 (C-4), 68.77, 68.28, 62.89 (C-6), 54.22 (OCH$_3$). HRMS m/z calcd for C$_{28}$H$_{35}$N$_8$O$_{10}$S (M+H$^+$), 675.2197; found, 675.2202.

S4c) 3,3'-Dideoxy-3,3'-bis-[4-(1-methyl-1H-imidazol-5-yl)-1H-1,2,3-triazol-1-yl]-1,1'-sulfanediyl-di-β-D-galactopyranoside White amorphous solid. $^1$H NMR (CD$_3$OD, 400 MHz) δ: 8.40 (s, 2H, triazole-H), 7.71 (s, 2H, imidazole-H), 7.23 (s, 2H, imidazole-H), 4.92 (6H, obscured under H$_2$O, H-1, H-2, H-3), 4.14 (d, 2H, 2.4 Hz, H-4), 3.88 (m, 12H, NCH$_3$, H-5, H-6). $^{13}$C NMR (DMSO, 100 MHz) δ: 140.77, 138.24, 128.24, 123.21, 86.83 (C-1), 81.43 (C-5), 69.73, 68.79, 68.28, 62.85, 33.62. HRMS m/z calcd for C$_{24}$H$_{33}$N$_{10}$O$_8$S (M+H$^+$), 621.2204; found, 621.2205.

S4d) 3,3'-Dideoxy-3,3'-bis-[4-(3-chloro-5-trifluoromethyl-pyridin-2-yl)-1H-1,2,3-triazol-1-yl]-1,1'-sulfanediyl-di-β-D-galactopyranoside White amorphous solid. $^1$H NMR (DMSO, 400 MHz) β: 9.02 (d, 2H, 1.2 Hz, ArH), 8.71 (s, 2H, triazole-H), 8.57 (d, 2H, 1.6 Hz, ArH), 5.54 (d, 2H, 6.0 Hz, OH), 5.36 (d, 2H, 7.2 Hz, OH), 4.99 (m, 4H, H-3, H-1), 4.75 (t, 2H, OH), 4.27 (t, 2H, $J_{2,3}$ 10.0 Hz, H-2), 4.01 (d, 2H, $J_{3,4}$ 2.8 Hz, H-4), 3.77 (m, 2H, H-5), 3.57 (m, 4H, H-6). $^{13}C$ NMR (DMSO, 100 MHz) δ: 150.90, 144.94, 143.76, 136.93, 128.69, 126.76, 125.22, 124.65, 121.94, 83.96 (C-1), 79.77 (C-5), 68.05 (C-4), 67.54 (C-3), 67.27 (C-2), 60.65 (C-6). HRMS m/z calcd fro $C_{28}H_{26}N_8O_8SCl_2F_6Na$ (M+Na$^+$), 841.0073; found, 841.0078.

s4e) 3,3'-Dideoxy-3,3'-bis-[4-(pyrimidin-5-yl)-1H-1,2,3-triazol-1-yl]-1,1'-sulfanediyl-di-β-D-galactopyranoside White amorphous solid. $^1$H NMR (DMSO, 400 MHz) δ: 9.28 (s, 4H, triazole-H, ArH), 9.16 (s, 2H, ArH), 8.88 (s, 2H, ArH), 5.44 (m, 4H, OH), 4.96 (m, 4H, H-3, H-1), 4.73 (t, 2H, OH), 4.27 (t, 2H, $J_{2,3}$ 10.0 Hz, H-2), 3.99 (d, 2H, $J_{3,4}$ 2.8 Hz, H-4), 3.76 (m, 2H, H-5), 3.57 (m, 4H, H-6). $^{13}C$ NMR (DMSO, 100 MHz) δ: 160.34, 157.46, 153.10, 139.90, 125.33, 125.52, 83.56 (C-1), 79.23 (C-5), 67.43, 67.23, 66.98, 60.21 (C-6). HRMS m/z calcd for $C_{24}H_{28}N_{10}O_8SNa$ (M+Na$^+$), 639.1710; found, 639.1715.

s4f) 3,3'-Dideoxy-3,3'-bis-[4-(pyridin-2-yl)-1H-1,2,3-triazol-1-yl]-1,1'-sulfanediyl-di-β-D-galactopyranoside White amorphous solid. $^1$H NMR (CD$_3$OD, 400 MHz) δ: 8.66 (s, 2H, triazole-H), 8.53 (d, 2H, 4.4 Hz, ArH), 8.06 (d, 2H, 7.6 Hz, ArH), 7.90 (t, 2H, 8.0 Hz, 7.6 Hz, ArH), 7.35 (t, 2H, 6.0 Hz, 6.4 Hz, ArH), 4.97 (m, 4H, H-3, H-1), 4.73 (t, 2H, $J_{2,3}$ 10.4 Hz, H-2), 4.19 (d, 2H, 2.4 Hz, H-4), 3.92 (m, 4H, H-5, H-6), 3.74 (m, 2H, H-6). $^{13}C$ NMR (CD$_3$OD, 100 MHz) δ: 149.77, 148.99, 146.66, 137.59, 123.04, 122.46, 120.24, 85.09 (C-1), 80.01 (C-5), 68.33, 67.57, 65.90, 61.37 (C-6). HRMS m/z calcd for $C_{26}H_{31}N_8O_8S$ (M+H$^+$), 615.1986; found, 615.1988.

Synthesis Scheme for Compound S7;

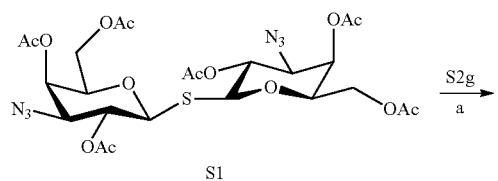

S1

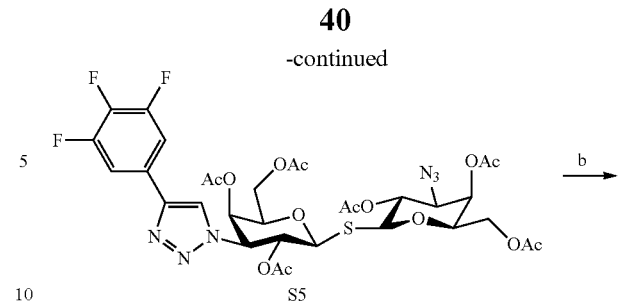

S5

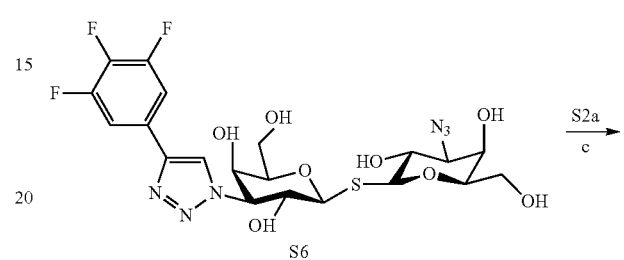

S6

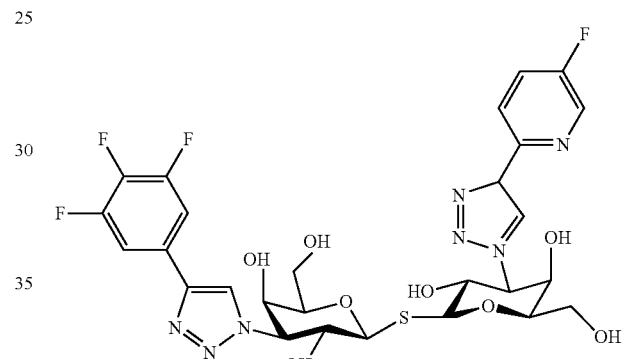

S7

(a) CuI, Et$_3$N, dry DMF, rt, N$_2$ atm; (b) 0.5M NaOMe in MeOH, rt

Synthesis of Example S7

| IUPAC name | Alkyne step a | Alkyne 2 | Example | Yield (%) |
|---|---|---|---|---|
| 3,3'-Dideoxy-3-[4-(5-fluoro-2-pyridin-2-yl)-1H-1,2,3-triazol-1-yl]-3'-[4-(3,4,5-trifluorophenyl)-1H-1,2,3-triazol-1-yl]1,1'-sulfanediyl-di-β-D-galactopyranoside | S2g | S2a | S7 | 84 | a) A solution of carbohydrate azide (S1) (300 mg, 0.454 mmol), Alkyne (S2g) (70 mg, 0.454 mmol), CuI (4.3 mg, 0.022 mmol) in dry DMF (10 mL) in a 25 mL round bottomed flask was stirred under nitrogen for 1 hour. Et$_3$N (0.031 mL, 0.227 mmol) was then added slowly via syringe. The resulting solution was allowed to stir at room temperature for 12 hours when TLC showed complete conversion of the starting carbohydrate azide (1:2, n-heptane-EtOAc). Solvents were evaporated in vacuo and the residue was dissolved in CH$_2$Cl$_2$ (10 mL) and washed successively with aqueous NH$_4$Cl (2×10 mL) and brine (10 mL). The organic layer was separated, dried (Na$_2$SO$_4$) and evaporated in vacuo. The residue was purified by flash chromatography using n-heptane-EtOAc as eluent to afford pure acetylated glycosylated triazole (S5) in 41% yield.

b) S5 was then deprotected using 0.5M NaOMe in MeOH and after the reaction was complete, it was neutralized using DOWEX H$^+$ resin. The resin was filtered and the crude was purified by flash chromatography using CH$_2$Cl$_2$:MeOH as eluent. This afforded the white amorphous compound S6 in 85% yield.

c) Compound S6 (76 mg, 0.093 mmol), Alkyne (S2a) (16.9 mg, 0.139 mmol), CuI (0.88 mg, 0.0046 mmol) in dry DMF (5 mL) was stirred under nitrogen for 1 hour. Et$_3$N (6.0 µL, 0.046 mmol) was then added slowly via syringe. The resulting solution was allowed to stir at room temperature for 12 hours when TLC showed complete conversion of the starting carbohydrate azide (6:1 CH$_2$Cl$_2$:MeOH). Solvents were evaporated in vacuo and the residue was purified by flash chromatography using CH$_2$Cl$_2$:MeOH as eluent to afford pure glycosylated triazole (1d) in 84% yield.

White amorphous solid. $^1$H NMR (CD$_3$OD, 400 MHz) δ: 8.63, 8.59 (2s, 2H, triazole-H), 8.47 (bs, 1H, Ar—H), 8.09 (bs, 1H, Ar—H), 7.72 (m, 1H, Ar—H). 7.63 (m, 1H, Ar—H) 4.95-4.91 (m, 3H, H1, H1', H3), 4.75-4.63 (m, 3H, H2, H2', H3'), 4.17 (dd, 2H, H4, H4'), 3.91-3.80 (m, 4H, H5, H5', H6, H6'), 3.73-3.69 (m, 2H, H6, H6'). $^{13}$C NMR (CD$_3$OD, 100 MHz) δ: 154.14, 151.67, 151.57, 147.92, 147.66, 145.52, 141.73, 139.24, 138.77, 138.52, 128.09, 125.51, 125.31, 123.74, 122.79, 122.57, 110.82, 110.75, 110.65, 110.59, 86.61 (C-1), 86.52 (C-1'), 81.42 (C-5), 81.35 (C-5'), 69.77, 69.64, 68.92, 68.89, 68.44, 68.37, 62.81, 62.77. HRMS m/z calcd for C$_{27}$H$_{27}$N$_7$O$_8$SF$_4$.

Synthesis of Examples S8a-h

S8a) 3,3'-3-[4-(pyridin-3-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside

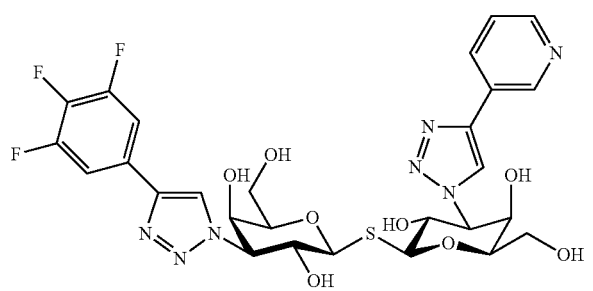

t (69 mg) and 3-ethynylpyridine (30 mg) was dissolved in MeCN (5 mL, dry) and stirred at r.t. Copper(I) iodide (8 mg) was added followed by Hünig's base (55 µL) and the mixture was heated to 50° C. After 18 h the mixture was filtered and concentrated. The residue was purified by HPLC (C$_{18}$/MeCN:H$_2$O:0.1% TFA). Freeze drying afforded the title compound as a white solid (65 mg). $^1$H NMR (400 MHz, Methanol-d$_4$) δ 9.21 (bs, 1H), 8.79 (s, 1H), 8.69 (bs, 1H), 8.68 (d, J=8.2 Hz, 1H), 8.57 (s, 1H), 7.88 (bs, 1H), 7.65-7.56 (m, 2H), 4.99-4.90 (m, 4H), 4.75-4.65 (m, 2H), 4.22-4.14 (m, 2H), 3.92-3.81 (m, 4H), 3.75-3.72 (m, 2H). ESI-MS m/z calcd for [C$_{27}$H$_{29}$F$_3$N$_7$O$_8$S]$^+$ (M+H)$^+$: 668.17; found: 668.25.

S8b) 3,3'-Dideoxy-3-[4-(1,3-pyrimidin-5-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside

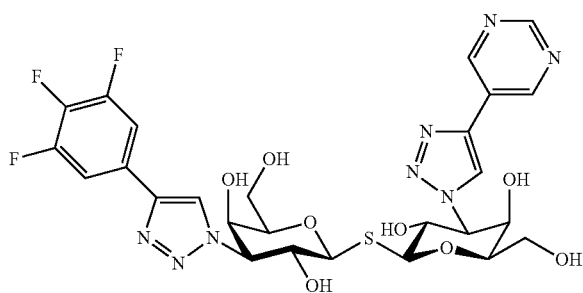

Intermediate 1 (92 mg) and 5-[2-(trimethylsilyl)ethynyl]-pyridine (65 mg) was dissolved in MeCN (5 mL, dry) and stirred at r.t. Copper(I) iodide (24 mg) was added followed by Hünig's base (65 µL) and the mixture was heated to 50° C. After 18 h cesium fluoride (5 mg) was added and the temperature increased to 70° C. After 24 h the mixture was filtered and concentrated. The residue was purified by HPLC (Xterra/MeCN:H$_2$O:25 mM NH$_3$). Freeze drying afforded the title compound as a white solid (73 mg). $^1$H NMR (400 MHz, Methanol-d$_4$) δ 9.25 (s, 2H), 9.13 (s, 1H), 8.76 (s, 1H), 8.58 (s, 1H), 7.65-7.56 (m, 2H), 5.01-4.88 (m, 4H), 4.75 (q, J=10.3 Hz, 2H), 4.17 (dd, J=8.7, 2.4 Hz, 2H), 3.95-3.78 (m, 4H), 3.73 (dd, J=11.3, 3.5 Hz, 2H). ESI-MS m/z calcd for [C$_{26}$H$_{28}$F$_3$N$_8$O$_8$S]$^+$ (M+H)$^+$: 669.16; found: 669.15.

S8c) 3,3'-Dideoxy-3-[4-(1,3-pyrimidin-2-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside

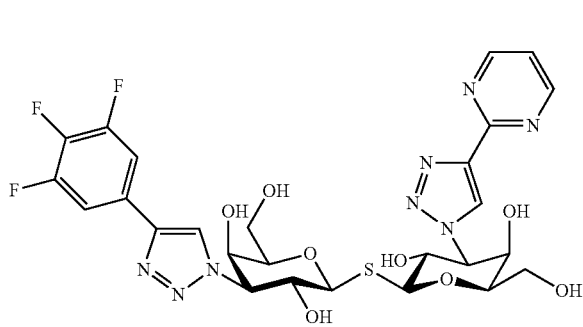

Intermediate 1 (71 mg) and 2-[2-(trimethylsilyl)ethynyl]-pyridine (48 mg) was dissolved in MeCN (5 mL, dry) and stirred at r.t. Copper(I) iodide (19 mg) was added followed by Hünig's base (50 µL) and the mixture was heated to 50°

C. After 18 h cesium fluoride (5 mg) was added and the temperature increased to 70° C. After 24 h the mixture was filtered and concentrated. The residue was purified by HPLC (Xterra/MeCN:H$_2$O:25 mM NH$_3$). Freeze drying afforded the title compound as a white sold (47 mg). $^1$H NMR (400 MHz, Methanol-d$_4$) δ 8.83 (bs, 2H), 8.59 (s, 1H), 7.65-7.56 (m, 2H), 7.42 (bs, 1H), 4.98-4.87 (m, 4H), 4.77-4.69 (m, 2H), 4.23-4.12 (m, 2H), 3.92-3.80 (m, 4H), 3.75-3.70 (m, 2H). ESI-MS m/z calcd for [C$_{26}$H$_{28}$F$_3$N$_8$O$_8$S]$^+$ (M+H)$^+$: 669.16; found: 669.15.

S8d) 3,3'-Dideoxy-3-[4-(pyridin-2-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside

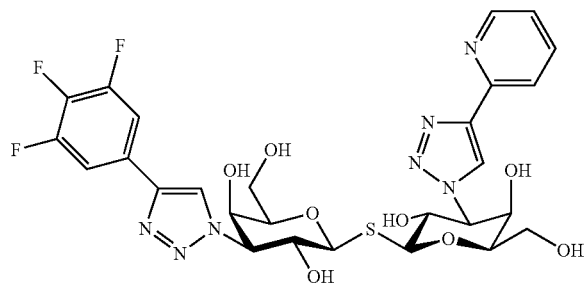

Intermediate 1 (50 mg), 2-ethynylpyridine (50 mg) and copper(I) iodide (9 mg) were mixed and degassed (argon) in acetonitrile (6 mL). Hünig's base (100 μl) was added and the mixture was stirred at r.t. over night. It was then concentrated and purified by flash chromatography (SiO$_2$/Petroleum ether:EtOAc 95:5→5:95). The appropriate fractions were concentrated and the residue dissolved in methanol (10 mL). NaOMe (1M in MeOH, 1.0 mL) was added and the mixture stirred 2 h. TFA (0.2 mL) was added and the mixture concentrated in vacuo. The residue was purified by HPLC (C$_{18}$/MeCN:H$_2$O:0.1% TFA). Freeze drying afforded the title compound as a white solid (13 mg). $^1$H NMR (400 MHz, Methanol-d$_4$) δ 8.65 (s, 1H), 8.60 (s, 1H), 8.56 (s, 1H), 8.09 (s, 1H), 7.93 (d, J=8.0 Hz, 1H), 7.66-7.54 (m, 2H), 7.37 (s, 1H), 4.97-4.87 (m, 4H), 4.74 (q, J=10.7 Hz, 2H), 4.16 (d, J=9.9 Hz, 2H), 3.94-3.78 (m, 4H), 3.71 (dt, J=10.5, 4.8 Hz, 2H). ESI-MS m/z calcd for [C$_{27}$H$_{29}$F$_3$N$_7$O$_8$S]$^+$ (M+H)$^+$: 668.17; found: 668.15.

S8c) 3,3'-Dideoxy-3-[4-(pyridin-4-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside

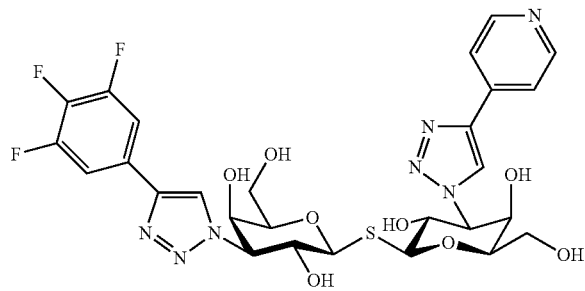

4-Ethynylpyridine hydrochloride (104 mg) was suspended in MeCN (10 mL) while bubbling argon through. Hünig's base (130 μL) was added and the mixture stirred 10 min. Intermediate 2 (45 mg) and copper(I) iodide (6 mg) were added and the mixture stirred 5 min. More Hünig's base (130 μl) was added, the vial closed and stirred at r.t. over night. The mixture was concentrated in vacuo, dissolved in EtOAc and filtered through a small plug of silica. The filtrate was concentrated and the residue dissolved in methanol (10 mL). NaOMe (1M in MeOH, 0.5 mL) was added and the mixture stirred at r.t. 2 h. TFA (0.2 mL) was added and the mixture concentrated in vacuo. The residue was purified by HPLC (Xterra/MeCN:H$_2$O:25 mM NH$_3$). Freeze drying afforded a white solid (5 mg). $^1$H NMR (400 MHz, Methanol-d4) δ 9.01 (s, 1H), 8.76 (d, J=6.2 Hz, 2H), 8.56 (s, 1H), 8.34 (d, J=6.2 Hz, 2H), 7.65-7.57 (m, 2H), 5.08-4.89 (m, 4H, 4.68 (td, J=10.1, 5.2 Hz, 2H), 4.18 (t, J=3.8 Hz, 2H), 3.86 (ddt, J=24.8, 13.3, 6.4 Hz, 4H), 3.73 (dt, J=11.3, 4.2 Hz, 2H). ESI-MS m/z calcd for [C$_{27}$H$_{29}$F$_3$N$_7$O$_8$S]$^+$ (M+H)$^+$: 668.17; found: 668.25.

S8f) 3-[4-((2-acetamid-N-yl)-pyridin-5-yl)-3,3'-dideoxy-1H-1,2,3-triazol-1-yl]-3'-[4-(3,4,5-trifluorophenyl)-1H-1,2,3-triazol-1-yl]-1,1'-sulfanediyl-di-β-D-galactopyranoside

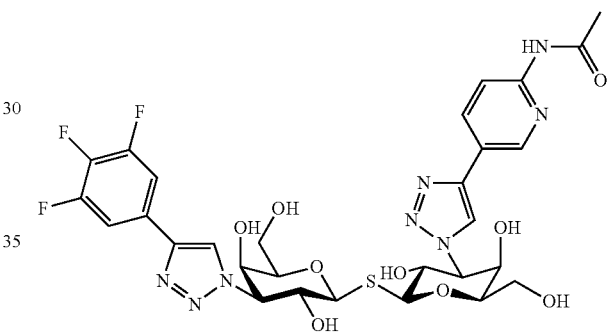

Intermediate 2 (40 mg) was dissolved in MeCN (10 mL, dry) and 5-ethynyl-2-pyridinamine (12 mg) was added and the mixture was stirred at r.t. under argon. Copper(I) iodide (5 mg) was added followed by Hünig's base (10 μL). After 18 h 5-ethynyl-2-pyridinamine (12 mg) was added and after an additional 6 h the mixture was filter and concentrated down. The residue was dissolved in MeOH (10 mL, dry) and NaOMe (1M in MeOH, 0.50 mL) was added and the mixture was stirred at r.t. After 18 h HOAc (1 mL) was added and the mixture concentrated down. The residue was purified by HPLC (C$_{18}$/MeCN:H$_2$O:0.1% TFA). Freeze drying afforded a white fluffy solid (15 mg). The material was dissolved in pyridine (2.5 mL) and Acetic anhydride (2.0 mL) was added and the mixture was stirred at r.t. After 18 h the mixture was concentrated down and purified by flash chromatography (SiO$_2$/Petroleum ether:EtOAc 95:5→0:100). The residue was dissolved in MeOH (5 mL, dry) and NaOMe (1M in MeOH, 0.25 mL) was added and the mixture was stirred at r.t. After 1 h CH$_2$Cl$_2$ (5 mL) and NaOMe (1M in MeOH, 0.25 mL) was added and after an additional 30 min HOAc (1 mL) was added and the mixture was concentrated down. The residue was purified by HPLC (C$_{18}$/MeCN:H$_2$O:0.1% TFA). Freeze drying afforded a white fluffy solid (4 mg). $^1$H NMR (400 MHz, Methanol-d$_4$) δ 8.79-8.73 (m, 1H), 8.62-8.56 (m, 3H), 8.24 (d, J=7.7 Hz, 1H), 8.08 (s, 1H), 7.63-7.56 (m, 2H), 4.93-4.72 (m, 6H), 4.20-4.13 (m, 2H), 3.92-3.78 (m, 4H), 3.72 (dd, J=11.1, 3.9 Hz, 2H), 2.20 (s, 3H). ESI-MS m/z calcd for [C$_{29}$H$_{32}$F$_3$N$_8$O$_9$S]$^+$ (M+H)$^+$: 725.19; found: 725.20.

S8g) 3-[4-(2-aminopyridin-5-yl)-3,3'-dideoxy-1H-1,2,3-triazol-1-yl]-3'-[4-(3,4,5-trifluorophenyl)-1H-1,2,3-triazol-1-yl]-1,1'-sulfanediyl-di-β-D-galactopyranoside

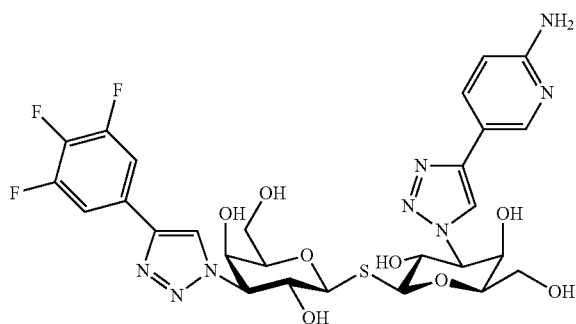

Intermediate 2 (40 mg) was dissolved in MeCN (7 mL, dry) and 5-ethynyl-2-pyridinamine (21 mg) was added and the mixture was stirred at r.t. under argon. Copper(I) iodide (18 mg) was added followed by Hünig's base (25 µL) and the mixture was heated to 27° C. After 18 h 5-ethynyl-2-pyridinamine (18 mg) was added and the temperature increased to 35° C. After an additional 2 h copper(I) iodide (5 mg) was added followed by Hünig's base (25 µL). After 5 h the temperature was lowered to 27° C., MeCN (7 mL, dry) was added followed by 5-ethynyl-2-pyridinamine (41 mg), copper(I) iodide (32 mg), and Hünig's base (50 µL). The mixture was stirred for 18 h and then concentrated down and purified by flash chromatography (SiO$_2$/Petroleum ether:EtOAc 95:5→0:100). The residue was dissolved in MeOH (10 mL, dry) and NaOMe (1M in MeOH, 0.50 mL) was added and the mixture was stirred at r.t. After 2 h HOAc (1 mL) was added and the mixture was concentrated down. The residue was purified by HPLC (C$_{18}$/MeCN:H$_2$O:0.1% TFA). Freeze drying afforded a white fluffy solid (10 mg). $^1$H NMR (400 MHz, Methanol-d$_4$) δ 8.55 (d, J=2.5 Hz, 2H), 8.33-8.26 (m, 2H), 7.66-7.57 (m, 2H), 7.08 (d, J=9.9 Hz, 1H), 4.97-4.86 (m, 4H), 4.69-4.57 (m, 2H), 4.19-4.13 (m, 2H), 3.93-3.79 (m, 4H), 3.77-3.67 (m, 2H). ESI-MS m/z calcd for [C$_{27}$H$_{30}$F$_3$N$_8$O$_8$S]$^+$ (M+H)$^+$: 683.13; found: 683.10.

S8h) 3,3'-Dideoxy-3-[4-(5-fluoro-1,3-pyrimidin-2-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside

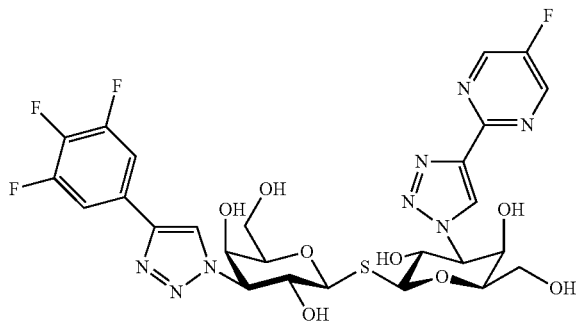

2-Chloro-5-fluoro-pyrimidine (1.0 mL) was dissolved in DME (10 mL). TMS-Br (1.5 mL) was added and the mixture stirred at 150° C. in a closed vial for 1.5 h. The mixture was allowed to cool, then concentrated in vacuo. The residue was dissolved in CH$_2$Cl$_2$ and filtered through a plug of silica. The filtrate was concentrated in vacuo to give a pale yellow liquid (1.54 g). This compound, 2-bromo-5-fluoropyrimidine (containing some 2-chloro-5-fluoro-pyrimidine), (0.75 g) was dissolved in triethylamine (7 mL) under an argon atmosphere. TMS-acetylene (0.6 mL) was added followed by bis(triphenylphosphine)palladium(II) dichloride (15 mg) and copper(I) iodide (30 mg). After heating the mixture at 50° C. 5 h, it was concentrated in vacuo. The residue was purified by flash chromatography (SiO$_2$/Petroleum ether:EtOAc 95:5→5:95) and 5-fluoro-2-[2-(trimethylsilyl)ethynyl]pyrimidine was isolated as a colorless oil (300 mg, 38% purity).

5-Fluoro-2-[2-(trimethylsilyl)ethynyl]pyrimidine (210 mg, 38% purity) was dissolved in MeCN (10 mL) while bubbling nitrogen through. TBAF (120 mg) was added. After 2 min, Intermediate 2 (67 mg) in acetonitrile (5 mL) and copper(I) iodide (8 mg) were added and the mixture stirred 5 min. Hünig's base (400 µL) was added, the vial closed and stirred at (room temperature) r.t. overnight and then at 50° C. for 24 h. The mixture was concentrated in vacuo and the residue filtered through silica (CH$_2$Cl$_2$:MeOH 9:1). Evaporation of the solvents in vacuo afforded a brown residue. This was dissolved in MeOH (15 mL) and NaOMe (1M in MeOH, 1 ml) was added and the mixture stirred for 2 h. TFA (0.2 mL) was added and the mixture concentrated in vacuo. The residue was purified by HPLC (C$_{18}$/MeCN:H$_2$O:0.1% TFA). Freeze drying afforded the product as an off-white power (32 mg). $^1$H NMR (400 MHz, Methanol-d4) δ 8.72 (d, J=3.1 Hz, 3H), 8.58 (d, J=1.8 Hz, 1H), 7.61 (t, J=7.6 Hz, 2H), 5.00-4.97 (m, 4H), 4.73 (q, J=9.5 Hz, 2H), 4.22-4.12 (m, 2H), 3.92-3.78 (m, 4H), 3.72 (d, J=10.9 Hz, 2H). ESI-MS m/z calcd for [C$_{26}$H$_{27}$F$_4$N$_8$O$_8$S]$^+$ (M+H)$^+$: 687.15; found: 687.15.

Synthesis of Intermediates to Examples S8a-h
Intermediate 1

3-Azido-3,3'-dideoxy-3'-[4-(3,4,5-trifluorophenyl)-1H-1,2,3-triazol-1-yl]-1,1'-sulfanediyl-di-β-D-galactopyranoside 2,2',4,4',5,5',6,6'-Hexa-O-acetyl-3,3'-diazido-3,3'-dideoxy-1,1'-sulfanediyl-di-β-D-galactopyranoside (131 mg) and trimethyl-[2-(3,4,5-trifluorophenyl)ethynyl]silane (45 µl) were mixed in acetonitrile (5 mL) and degassed (argon). Cesium fluoride (30 mg) was added and the mixture stirred 5 min. Copper(I) iodide (4 mg) was added, followed by Hünig's base (100 µl). The mixture was stirred at r.t. overnight and then concentrated in vacuo. It was then evaporated on to silica and purified by flash chromatography (SiO$_2$/Petroleum ether:EtOAc 95:5→5:95). The appropriate fractions were concentrated and the residue dissolved in methanol (10 mL). 1M sodium methoxide in methanol (1.5 ml) was added and the mixture stirred 2 h. TFA (0.2 ml) was added and the mixture concentrated in vacuo. The residue was purified by HPLC (C$_{18}$/MeCN:H$_2$O:0.1% TFA). Freeze drying afforded a white solid (61 mg).

Intermediate 2

2,2',4,4',5,5',6,6'-Hexa-O-acetyl-3-azido-3,3'-dideoxy-3'-[4-(3,4,5-trifluorophenyl)-1H-1,2,3-triazol-1-yl]-1,1'-sulfanediyl-di-β-D-galactopyranoside Intermediate 1 (150 mg) was dissolved in pyridine (5 mL). Acetic anhydride (0.50 mL) was added and mixture stirred overnight and then concentrated in vacuo. The residue was dissolved in $CH_2Cl_2$ (DCM) and filtered through silica (2 g), eluted with 2% MeOH in DCM. The filtrate was concentrated in vacuo to afford Intermediate 2 as a white solid (209 mg). $^1$H NMR (400 MHz, Methanol-$d_4$) δ 8.58 (d, J=1.2 Hz, 2H), 7.60 (dd, J=8.5, 6.5 Hz, 4H), 4.90 (d, J=3.3 Hz, 4H), 4.72 (t, J=10.1 Hz, 2H), 4.16 (d, J=2.8 Hz, 2H), 3.94-3.78 (m, 4H), 3.72 (dd, J=11.3, 4.4 Hz, 2H).

Intermediate 2, Alternative Synthesis 2,4,6-Tri-O-acetyl-3-azido-3-deoxy-α-D-galactopyranosyl bromide 1,2,4,6-Tetra-O-acetyl-3-azido-deoxy-β-D-galactopyranoside (1.99 g) and titanium tetrabromide (2.7 g) were mixed in EtOAc (100 ml) and stirred at 27° C. 48 h. Washed with aq. 5% $NaHCO_3$ (100 ml) and brine (100 ml). Purification by flash chromatography ($SiO_2$/Petroleum ether:EtOAc 95:5→5:95) afforded 2.01 g of 2,4,6-tri-O-acetyl-3-azido-3-deoxy-α-D-galactopyranosyl bromide. $^1$H NMR (400 MHz, Chloroform-d) δ 6.71 (d, J=3.8 Hz, 1H), 5.50 (d, J=2.5 Hz, 1H), 4.95 (dd, J=10.6, 3.8 Hz, 1H), 4.42 (t, J=6.4 Hz, 1H), 4.22-4.03 (m, 3H), 2.18 (s, 3H), 2.17 (s, 3H), 2.08 (s, 3H).

Tri-isopropylsilyl 2,4,6-tri-O-acetyl-3-azido-3-deoxy-1-thio-β-D-galactopyranoside 2,4,6-Tri-O-acetyl-3-azido-3-deoxy-α-D-galactopyranosyl bromide (370 mg) was dissolved in MeCN (15 mL, dry) and stirred at r.t. under argon for five minutes. $K_2CO_3$ (390 mg, dry) was added followed by TIPSSH (305 µL). After 200 minutes the mixture was concentrated down, re-dissolved in $CH_2Cl_2$ and washed twice with water. The water phase was extracted once with $CH_2Cl_2$ and the combined organic phase was dried (phase separator) and concentrated. Purification by flash chromatography ($SiO_2$/Petroleum ether:EtOAc 100:0→50:50) afforded 312 mg of tri-isopropylsilyl 2,4,6-tri-O-acetyl-3-azido-3-deoxy-1-thio-β-D-galactopyranoside. $^1$H NMR (400 MHz, Chloroform-d) δ 5.45 (d, J=2.5 Hz, 1H), 5.23 (t, J=9.8 Hz, 1H), 4.63 (d, J=9.5 Hz, 1H), 4.14 (dd, J=11.5, 5.5 Hz, 1H), 4.03 (dd, J=11.5, 7.2 Hz, 1H), 3.82 (t, J=6.3 Hz, 1H), 3.56 (dd, J=10.1, 3.3 Hz, 1H), 2.18 (s, 3H), 2.15 (s, 3H), 2.05 (s, 3H), 1.32-1.23 (m, 3H), 1.18-1.06 (m, 18H).

1,2,4,6-Tetra-O-acetyl-3-deoxy-3-[4-(3,4,5-trifluorophenyl)-1H-1,2,3-triazol-1-yl]-β-D-galactopyranoside Trimethyl-[2-(3,4,5-trifluorophenyl)ethynyl]silane (1120 µL) was dissolved in MeCN (50 mL, dry) and stirred at r.t. under argon and triethylamine trihydrofluoride (435 µL) was added. After 25 minutes 1,2,4,6-tetra-O-acetyl-3-azido-3-deoxy-β-D-galactopyranoside (1025 mg) was added followed by copper(I) iodide (138 mg) and Hünig's base (2.00 mL). After 18 h brine was added and the mixture was extracted three times with ether. The organic phase was washed once with brine, dried ($Na_2SO_4$) and concentrated. Re-crystallization from EtOH afforded 1.19 g of 1,2,4,6-tetra-O-acetyl-3-deoxy-3-[4-(3,4,5-trifluorophenyl)-1H-1,2,3-triazol-1-yl]-β-D-galactopyranoside. $^1$H NMR (400 MHz, Chloroform-d) δ 7.80 (s, 1H), 7.47-7.38 (m, 2H), 5.86 (d, J=9.1 Hz, 2H), 5.58 (d, 1H), 5.19 (d, J=9.2 Hz, 1H), 4.30-4.08 (m, 3H), 2.18 (s, 3H), 2.08 (s, 3H), 2.06 (s, 3H), 1.91 (s, 3H). ESI-MS m/z calcd for $[C_{22}H_{23}F_3N_3O_9]^+$ (M+H)$^+$: 530.1; found 530.1.

2,4,6-Tri-O-acetyl-3-deoxy-3-[4-(3,4,5-trifluorophenyl)-1H-1,2,3-triazol-1-yl]-α-D-galactopyranosyl bromide 1,2,4,6-tetra-O-acetyl-3-deoxy-3-[4-(3,4,5-trifluorophenyl)-1H-1,2,3-triazol-1-yl]-β-D-galactopyranoside (273 mg) was suspended in $CH_2Cl_2$/AcOH (1:1, 4 mL) and stirred at r.t. Acetic anhydride (1 mL) was added followed by HBr (33% in AcOH, 2 mL). After 20 h excess HBr was purged away with argon and the mixture was concentrated. Purification by flash chromatography ($SiO_2$/Petroleum ether:EtOAc 95:5→5:95) afforded 263 mg of 2,4,6-tri-O-acetyl-3-deoxy-3-[4-(3,4,5-trifluorophenyl)-1H-1,2,3-triazol-1-yl]-α-D-galactopyranosyl bromide. $^1$H NMR (400 MHz, Chloroform-d) δ 7.79 (s, 1H), 7.49-7.40 (m, 2H), 6.89 (d, J=3.8 Hz, 1H), 5.82 (dd, J=11.4, 3.9 Hz, 1H), 5.63 (s, 1H), 5.32 (d, J=11.2 Hz, 1H), 4.65 (t, J=6.5 Hz, 1H), 4.25 (dd, J=11.7, 6.3 Hz, 1H), 4.15 (dd, J=11.9, 6.4 Hz, 1H), 2.07 (s, 6H), 1.97 (s, 3H). ESI-MS m/z calcd for $[C_{20}H_{20}BrF_3N_3O_7]^+$ (M+H)$^+$: 550.0; found: 550.0.

2,2',4,4',5,5',6,6'-Hexa-O-acetyl-3-azido-3,3'-dideoxy-3'-[4-(3,4,5-trifluorophenyl)-1H-1,2,3-triazol-1-yl]-1,1'-sulfanediyl-di-β-D-galactopyranoside (Intermediate 2)

Tri-isopropylsilyl 2,4,6-tri-O-acetyl-3-azido-3-deoxy-1-thio-β-D-galactopyranoside (308 mg) was dissolved in MeCN (10 mL, dry) and stirred at r.t. under argon. 2,4,6-Tri-O-acetyl-3-deoxy-3-[4-(3,4,5-trifluorophenyl)-1H-1,2,3-triazol-1-yl]-α-D-galactopyranosyl bromide (405 mg) dissolved in MeCN (10 mL, dry) was added. After five minutes TBAF (235 mg) dissolved in MeCN (5 mL, dry) was added. After two minutes the mixture was cooled to 0° C. and after another three minutes the mixture was concentrated. Purification by flash chromatography ($SiO_2$/Petroleum ether:EtOAc 100:0→0:100) afforded 262 mg of 2,2',4,4',5,5',6,6'-hexa-O-acetyl-3-azido-3,3'-dideoxy-3'-[4-(3,4,5-trifluorophenyl)-1H-1,2,3-triazol-1-yl]-1,1'-sulfanediyl-di-β-D-galactopyranoside. $^1$H NMR (400 MHz, Chloroform-d) δ 7.83 (s, 1H), 7.47-7.41 (m, 2H), 5.74 (t, J=10.4 Hz, 1H), 5.62 (d, J=2.4 Hz, 1H), 5.51 (d, J=2.3 Hz, 1H), 5.24 (t, J=10.0 Hz, 2H), 5.17 (dd, J=10.9, 3.1 Hz, 1H), 4.97 (d, J=9.8 Hz, 1H), 4.83 (d, J=9.9 Hz, 1H), 4.21 (dt, J=21.3, 5.6 Hz, 6H), 4.15-4.07 (m, 2H), 3.92 (t, J=6.4 Hz, 1H), 3.68 (dd, J=10.0, 3.3 Hz, 1H), 2.20 (s, 3H), 2.17 (s, 3H), 2.12 (s, 3H), 2.09 (s, 3H), 2.07 (s, 3H), 1.93 (s, 3H). ESI-MS m/z calcd for $[C_{32}H_{36}F_3N_6O_{14}S]^+$ (M+H)$^+$: 817.2; found: 817.2.

REFERENCES

Almkvist, J., Fäldt, J., Dahlgren, C., Leffler, H., and Karlsson, A. (2001) Lipopolysaccharide-induced gelatinase granule mobilization primes neutrophils for activation by galectin-3 and f-Met-Leu-Phe. *Infect. Immun.* Vol. 69: 832-837.

Barondes, S. H., Cooper, D. N. W., Gitt, M. A., and Leffler, H. (1994). Galectins, Structure and function of a large family of animal lectins. *J. Biol. Chem.* 269:20807-20810.

Blois, S. M., Ilarregui, J. M., Tometten, M., Garcia, M., Orsal, A. S., Cordo-Russo, R., Toscano, M. A., Bianco, G. A., Kobelt, P., Handjiski, B., et al. (2007). A pivotal role for galectin-1 in fetomaternal tolerance. *Nat Med* 13: 1450-1457.

Chen, W.-S., Leffler H., Nilsson, U. J., Panjwani, N. (2012). Targeting Galectin-1 and Galectin-3 Attenuates VEGF-A-induced Angiogenesis; *Mol. Biol. Cell* (suppl), Abstract No. 2695.

Cumpstey, I., Carlsson, S., Leffler, H. and Nilsson, U. J. (2005) Synthesis of a phenyl thio-β-D-galactopyranoside library from 1,5-difluoro-2,4-dinitrobenzene: discovery of efficient and selective monosaccharide inhibitors of galectin-7. *Org. Biomol. Chem.* 3: 1922-1932.

Cumpstey, I., Sundin, A., Leffler, H. and Nilsson, U. J. (2005) $C_2$-Symmetrical thiodigalactoside bis-benzamido derivatives as high-affinity inhibitors of galectin-3: Efficient lectin inhibition through double arginine-arene interactions. *Angew. Chem. Int. Ed.* 44: 5110-5112.

Cumpstey, I., Salomonsson, E., Sundin, A., Leffler, H. and Nilsson, U. J. (2008) Double affinity amplification of galectin-ligand interactions through arginine-arene interactions: Synthetic, thermodynamic, and computational studies with aromatic diamido-thiodigalactosides. *Chem. Eur. J.* 14: 4233-4245.

Dam, T. K., and Brewer, C. F. (2008). Effects of clustered epitopes in multivalent ligand-receptor interactions. *Biochemistry* 47: 8470-8476.

Delacour, D., Greb, C., Koch, A., Salomonsson, E., Leffler, H., Le Bivic, A., and Jacob, R. (2007). Apical Sorting by Galectin-3-Dependent Glycoprotein Clustering. *Traffic* 8: 379-388.

Delaine, T., Cumpstey, I., Ingrassia, L., Le Mercier, M., Okechukwu, P., Leffler, H., Kiss, R., and Nilsson, U. J. (2008). Galectin-Inhibitory Thiodigalactoside Ester Derivatives Have Anti-Migratory Effects in Cultured Lung and Prostate Cancer Cells. *J Med Chem* 51; 8109-8114.

Garner, O. B., and Baum, L. G. (2008). Galectin-glycan lattices regulate cell-surface glycoprotein organization and signalling. *Biochem Soc Trans* 36: 1472-1477.

Giguere, D., Patnam, R., Bellefleur, M.-A., St.-Pierre, C., Sato, S., and Roy, R. (2006). Carbohydrate triazoles and isoxazoles as inhibitors of galectins-1 and -3. *Chem Commun:* 2379-2381.

Glinsky, G. V., Price, J. E., Glinsky, V. V., Mossine, V. V., Kiriakova, G., and Metcalf, J. B. (1996). *Cancer Res* 56: 5319-5324.

Glinsky, V. V., Kiriakova, G., Glinskii, O. V., Mossine, V. V., Mawhinney, T. P., Turk, J. R., Glinskii, A. B., Huxley, V. H., Price, J. E., and Glinsky, G. V. (2009). Synthetic Galectin-3 Inhibitor Increases Metastatic Cancer Cell Sensitivity to Taxol-Induced Apoptosis In Vitro and In Vivo. *Neoplasia* 11; 901-909.

Huflejt, M. E. and Leffler, H. (2004) Galectin-4 in normal tissues and cancer. *Glycoconj. J.* 20: 247-255.

Ingrassia et al. (2006) A Lactosylated Steroid Contributes in Vivo Therapeutic Benefits in Experimental Models of Mouse Lymphoma and Human Glioblastoma. *J. Med. CHem.* 49: 1800-1807.

John, C. M., Leffler, H., Kahl-Knutsson, B., Svensson, I., and Jarvis, G. A. (2003) Truncated Galectin-3 Inhibits Tumor Growth and Metastasis in Orthotopic Nude Mouse Model of Human Brest *Cancer. Clin. Cancer Res.* 9: 2374-2383.

Lau, K. S., and Dennis, J. W. (2008). N-Glycans in cancer progression. *Glycobiology* 18: 750-760.

Lau, K. S., Partridge, E. A., Grigorian, A., Silvescu, C. I., Reinhold, V. N., Demetriou, M., and Dennis, J. W. (2007). Complex N-glycan number and degree of branching cooperate to regulate cell proliferation and differentiation. *Cell* 129: 123-134.

Leffler, H. and Barondes, S. H. (1986) Specificity of binding of three soluble rat lung lectins to substituted and unsubstituted mammalian beta-galactosides. *J. Biol. Chem.* 261: 10119-10126.

Leffler, H. Galectins Structure and Function—A synopsis in Mammalian Carbohydrate Recognition Systems (Crocker, P. ed.) Springer Verlag, Heidelberg, 2001 pp. 57-83.

Leffler, H., Carlsson, S., Hedlund, M., Qian, Y. and Poirier, F. (2004) Introduction to galectins. *Glycoconj. J.* 19: 433-440.

Leffler, H., editor, (2004b) Special Issue on Galectins. *Glyoconj. J.* 19: 433-638.

Lin, C.-I., Whang, E. E., Donner, D. B., Jiang, X., Price, B. D., Carothers, A. M., Delaine, T., Leffler, H., Nilsson, U. J., Nose, V., et al. (2009). Galectin-3 Targeted Therapy with a Small Molecule Inhibitor Activates Apoptosis and Enhances Both Chemosensitivity and Radiosensitivity in Papillary Thyroid Cancer. *Mol Cancer Res* 7: 1655-1662.

MacKinnon, A. C. Farnworth, S. L., Henderson, N. C., Hodkinson, P. S., Kipari, T., Leffler, H., Nilsson, U. J., Haslett, C., Hughes, J., and Sethi T. (2008). Regulation of alternative macrophage activation by Galectin-3. *J. Immun.* 180; 2650-2658.

Mackinnon, A., Gibbons, M., Farnworth, S., Leffler, H., Nilsson, U. J., Delaine, T., Simpson, A., Forbes, S., Hirani, N., Gauldie, J., and Sethi T. (2012). Regulation of TGF-β1 driven lung fibrosis by Galectin-3. *Am. J. Resp. Crit. Care Med.*, in press.

Massa, S. M., Cooper, D. N. W., Leffler, H., Barondes, S. H. (1993) L-29, an endogenous lectin, binds to glycoconjugate ligands with positive cooperativity. *Biochemistry* 32: 260-267.

Melero, I., Berman, D. M., Aznar, M. A., Korman, A. J., Gracia, J. L. P., Haanen, J. (2015) *Nature Reviews Cancer,* 15: 457-472

Partridge, E. A., Le Roy, C., Di Guglielmo, G. M., Pawling, J., Cheung, P., Granovsky, M., Nabi, I. R., Wrana, J. L., and Dennis, J. W. (2004). Regulation of cytokine receptors by Golgi N-glycan processing and endocytosis. *Science* 306: 120-124.

Perone, M. J., Bertera, S., Shufesky, W. J., Divito, S. J., Montecalvo, A., Mathers, A. R., Larregina, A. T., Pang, M., Seth, N., Wucherpfennig, K. W., et al. (2009). Suppression of autoimmune diabetes by soluble galectin-1. *J. Immunol* 182: 2641-2653.

Pienta, K. J., Naik, H., Akhtar, A., Yamazaki, K., Replogle, T. S., Lehr, J., Donat, T. L., Tait, L., Hogan, V., and Raz, A. (1995). Inhibition of spontaneous metastasis in a rat prostate cancer model by oral administration of modified citrus pectin. *J Natl Cancer Inst* 87, 348-353.

Saegusa, J., Hsu, D. K., Chen, H. Y., Yu, L., Fermin, A., Fung, M. A., and Liu, F. T. (2009). Galectin-3 is critical for the development of the allergic inflammatory response in a mouse model of atopic dermatitis. *Am J Pathol* 174: 922-931.

Salameh, B. A., Leffler, H. and Nilsson, U. J. (2005) *Bioorg. Med. Chem. Lett.* 15: 3344-3346.

Salameh, B. A., Cumpstey, I., Sundin, A., Leffler, H., and Nilsson, U. J. (2010). 1H-1,2,3-Triazol-1-yl thiodigalactoside derivatives as high affinity galectin-3 inhibitors. *Bioorg Med Chem* 18: 5367-5378.

Salomonsson, E., Larumbe, A., Tejler, J., Tullberg, E., Rydberg, H., Sundin, A., Khabut, A., Frejd, T., Lobsanov, Y. D., Rini, J. M., Nilsson, U. J., and Leffler, H (2010). Monovalent interactions of galectin-1. *Biochemistry* 49: 9518-9532.

Sörme, P., Qian, Y., Nyholm, P.-G., Leffler, H., Nilsson, U. J. (2002) Low micromolar inhibitors of galectin-3 based on 3'-derivatization of N-acetyllactosamine. *ChemBioChem* 3:183-189.

Sörme, P., Kahl-Knutsson, B., Wellmar, U., Nilsson, U. J., and Leffler H. (2003a) Fluorescence polarization to study galectin-ligand interactions. *Meth. Enzymol.* 362: 504-512.

Sörme, P., Kahl-Knutsson, B., Wellmar, U., Magnusson, B.-G., Leffler H., and Nilsson, U. J. (2003b) Design and synthesis of galectin inhibitors. *Meth. Enzymol.* 363: 157-169.

Sörme, P., Kahl-Knutsson, B., Huflejt, M., Nilsson, U. J., and Leffler H. (2004) Fluorescence polarization as an analytical tool to evaluate galectin-ligand interactions. *Anal. Biochem.* 334: 36-47.

Thijssen, V. L., Poirer, F., Baum, L. G., and Griffioen, A. W. (2007). Galectins in the tumor endothelium: opportunities for combined cancer therapy. *Blood* 110: 2819-2827.

Toscano, M. A., Bianco, G. A., Ilarregui, J. M., Croci, D. O., Correale, J., Hernandez, J. D., Zwirner, N. W., Poirier, F., Riley, E. M., Baum, L. G., et al. (2007). Differential glycosylation of TH1, TH2 and TH-17 effector cells selectively regulates susceptibility to cell death. *Nat Immunol* 8: 825-834.

We claim:

1. A 1,1'-sulfanediyl-di-β-D-galactopyranoside compound of formula (1)

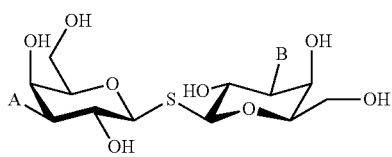

wherein
A is selected from a group of formula 2

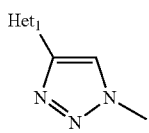

wherein Het1 is selected from a five or six membered heteroaromatic ring, optionally substituted with a group selected from Br, F, Cl, NH$_2$, NHC(=O)CH$_3$, methyl optionally substituted with a F, oxo, and OCH$_3$ optionally substituted with a F;

B is selected from a group of formula 3, 4 and 5

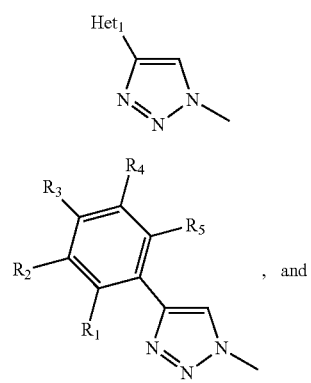

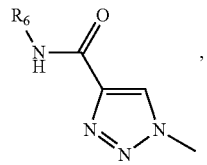

wherein Het2 is selected from a five or six membered heteroaromatic ring, optionally substituted with a group selected from Br, F, Cl, NH$_2$, NHC(=O)CH$_3$, methyl optionally substituted with a F, Oxo, and OCH$_3$ optionally substituted with a F, R$_1$-R$_5$ are independently selected from H, F, methyl optionally substituted with a fluorine (F), and OCH$_3$ optionally substituted with a F, R$_6$ is selected from C$_{1-6}$ alkyl, branched C$_{3-6}$ alkyl and C$_{3-7}$ cycloalkyl; or a pharmaceutically acceptable salt or solvate thereof.

2. The compound of claim 1, wherein A is selected from formula 2 and B is selected from formula 3.

3. The compound of claim 1, wherein A is selected from formula 2 and Het1 is selected from a five membered hetero aromatic ring containing 1-4 nitrogen atoms, optionally 1 oxygen atom and optionally one sulphur atom and a six membered hetero aromatic ring containing 1-4 nitrogen atoms; and B is selected from formula 3 and Het2 is selected from a five or six membered heteroaromatic ring, optionally substituted with a group selected from Br, F, Cl, methyl optionally substituted with a F, oxo, and OCH$_3$ optionally substituted with a F.

4. The compound of claim 1, wherein A is selected from formula 2 and Het1 is selected from a five or six membered heteroaromatic ring, optionally substituted with a group selected from Br, F, Cl, methyl optionally substituted with a F, oxo, and OCH$_3$ optionally substituted with a F; and B is selected from formula 3 and Het2 is selected from a five membered hetero aromatic ring containing 1-4 nitrogen atoms, optionally 1 oxygen atom and optionally one sulphur atom and a six membered hetero aromatic ring containing 1-4 nitrogen atoms.

5. The compound of claim 1, wherein A is selected from formula 2 and Het1 is selected from a five membered hetero aromatic ring containing 1-4 nitrogen atoms, optionally 1 oxygen atom and optionally one sulphur atom and a six membered hetero aromatic ring containing 1-4 nitrogen atoms; and B is selected from formula 3 and Het2 is selected from a five membered hetero aromatic ring containing 1-4 nitrogen atoms, optionally 1 oxygen atom and optionally one sulphur atom and a six membered hetero aromatic ring containing 1-4 nitrogen atoms.

6. The compound of claim 1, wherein A is selected from formula 2 and Het1 is selected from a five membered hetero aromatic ring containing 1-4 nitrogen atoms, optionally 1 oxygen atom and optionally one sulphur atom, substituted with a group selected from Br, F, Cl, CF$_3$, and OCH$_3$ and a six membered hetero aromatic ring containing 1-4 nitrogen atoms substituted with a group selected from Br, F, Cl, CF$_3$, oxo and OCH$_3$; and B is selected from formula 3 and Het2 is selected from a five or six membered heteroaromatic ring, optionally substituted with a group selected from Br, F, Cl, methyl optionally substituted with a F, oxo, and OCH$_3$ optionally substituted with a F.

7. The compound of claim 1, wherein A is selected from formula 2 and Het1 is selected from a five or six membered heteroaromatic ring, optionally substituted with a group selected from Br, F, Cl, oxo, $NH_2$, $NHC(=O)CH_3$, methyl optionally substituted with a F, and $OCH_3$ optionally substituted with a F; and B is selected from formula 3 and Het2 is selected from a five membered hetero aromatic ring containing 1-4 nitrogen atoms, optionally 1 oxygen atom and optionally one sulphur atom, substituted with a group selected from Br, F, Cl, $CF_3$, and $OCH_3$ and a six membered hetero aromatic ring containing 1-4 nitrogen atoms substituted with a group selected from Br, F, Cl, oxo, $CF_3$, and $OCH_3$.

8. The compound of claim 1, wherein A is selected from formula 2 and Het1 is selected from a five membered hetero aromatic ring containing 1-4 nitrogen atoms, optionally 1 oxygen atom and optionally one sulphur atom, substituted with a group selected from Br, F, Cl, $CF_3$, and $OCH_3$ and a six membered hetero aromatic ring containing 1-4 nitrogen atoms, substituted with a group selected from Br, F, Cl, oxo, $CF_3$, $NH_2$, $NHC(=O)CH_3$, and $OCH_3$; and B is selected from formula 3 and Het2 is selected from a five membered hetero aromatic ring containing 1-4 nitrogen atoms, optionally 1 oxygen atom and optionally one sulphur atom, substituted with a group selected from Br, F, Cl, $CF_3$, and $OCH_3$ and a six membered hetero aromatic ring containing 1-4 nitrogen atoms, substituted with a group selected from Br, F, Cl, oxo, $CF_3$, and $OCH_3$.

9. The compound of claim 1, wherein A is selected from formula 2 and B is selected from formula 4.

10. The compound of claim 1, wherein A is selected from formula 2 and Het1 is selected from a five membered hetero aromatic ring containing 1-4 nitrogen atoms, optionally 1 oxygen atom and optionally one sulphur atom, optionally substituted with a group selected from Br, F, Cl, $CF_3$, and $OCH_3$ and a six membered hetero aromatic ring containing 1-4 nitrogen atoms, optionally substituted with a group selected from Br, F, Cl, oxo, $CF_3$, $NH_2$, $NHC(=O)CH_3$, and $OCH_3$; and B is selected from formula 4 and $R_1$-$R_5$ are independently selected from H, F, methyl optionally substituted with a fluorine (F), and $OCH_3$ optionally substituted with a F, such as B is selected from formula 4 and $R_1$-$R_5$ are independently selected from H and F.

11. The compound of claim 1, wherein A is selected from formula 2 and B is selected from formula 5.

12. The compound of claim 1, wherein A is selected from formula 2 and Het1 is selected from a five membered hetero aromatic ring containing 1-4 nitrogen atoms, optionally 1 oxygen atom and optionally one sulphur atom, optionally substituted with a group selected from Br, F, Cl, $CF_3$, and $OCH_3$ and a six membered hetero aromatic ring containing 1-4 nitrogen atoms, optionally substituted with a group selected from Br, F, Cl, oxo, $CF_3$, and $OCH_3$; and B is selected from formula 5 and $R_6$ is selected from $C_{1-6}$ alkyl, branched $C_{3-6}$ alkyl and $C_{3-7}$ cycloalkyl.

13. The compound of claim 1, selected from:
- 3,3'-Dideoxy-3,3'-bis-[4-(5-fluoropyridin-2-yl)-1H-1,2,3-triazol-1-yl]-1,1'-sulfanediyl-di-β-D-galactopyranoside,
- 3,3'-Dideoxy-3,3'-bis-[4-(6-methoxypyridin-3-yl)-1H-1,2,3-triazol-1-yl]-1,1'-sulfanediyl-di-β-D-galactopyranoside,
- 3,3'-Dideoxy-3,3'-bis-[4-(1-methyl-1H-imidazol-5-yl)-1H-1,2,3-triazol-1-yl]-1,1'-sulfanediyl-di-β-D-galactopyranoside,
- 3,3'-Dideoxy-3,3'-bis-[4-(3-chloro-5-trifluoromethyl-pyridin-2-yl)-1H-1,2,3-triazol-1-yl]-1,1'-sulfanediyl-di-β-D-galactopyranoside,
- 3,3'-Dideoxy-3,3'-bis-[4-(pyrimidin-5-yl)-1H-1,2,3-triazol-1-yl]-1,1'-sulfanediyl-di-β-D-galactopyranoside,
- 3,3'-Dideoxy-3,3'-bis[4-(pyridin-2-yl)-1H-1,2,3-triazol-1-yl]-1,1'-sulfanediyl-di-β-D-galactopyranoside,
- 3,3'-Dideoxy-3-[4-(5-fluoropyridin-2-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside,
- 3,3'-Dideoxy-3-[4-(pyridin-3-yl)-1H-1,2,3-triazol-1-yl]-3-[4-(3,4,5-trifluorophenyl)-1H-1,2,3-triazol-1-yl]-1,1'-sulfanediyl-di-β-D-galactopyranoside,
- 3,3'-Dideoxy-3-[4-(1,3-pyrimidin-5-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside,
- 3,3'-Dideoxy-3-[4-(1,3-pyrimidin-2-yl)-1H-1,2,3-triazol-1-yl]-3-[4-(3,4,5-trifluorophenyl)-1H-1,2,3-triazol-1-yl]-1,1'-sulfanediyl-di-β-D-galactopyranoside,
- 3,3'-Dideoxy-3-[4-(pyridin-2-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside,
- 3,3'-Dideoxy-3-[4-(pyridin-4-yl)-1H-1,2,3-triazol-1-yl]-3-[4-(3,4,5-trifluorophenyl)-1H-1,2,3-triazol-1-yl]-1,1'-sulfanediyl-di-β-D-galactopyranoside,
- 3-[4-((2-acetamid-N-yl)-pyridin-5-yl)-3,3'-dideoxy-1H-1,2,3-triazol-1-yl]-3'-[4-(3,4,5-trifluorophenyl)-1H-1,2,3-triazol-1-yl]-1,1'-sulfanediyl-di-β-D-galactopyranoside,
- 3-[4-(2-aminopyridin-5-yl)-3,3'-dideoxy-1H-1,2,3-triazol-1-yl]-3'-[4-(3,4,5-trifluorophenyl)-1H-1,2,3-triazol-1-yl]-1,1'-sulfanediyl-di-β-D-galactopyranoside, and
- 3,3'-Dideoxy-3-[4-(5-fluoro-1,3-pyrimidin-2-yl)-1H-1,2,3-triazol-1-yl]-3'-[4-(3,4,5-trifluorophenyl)-1H-1,2,3-triazol-1-yl]-1,1'-sulfanediyl-di-β-D-galactopyranoside.

14. A pharmaceutical composition comprising the compound of claim 1 and optionally a pharmaceutically acceptable additive, such as carrier or excipient.

15. A method for treatment of a disorder relating to the binding of a galectin, to a ligand in a mammal, comprising administering a therapeutically effective amount of at least one compound according to claim 1 to a mammal in need of said treatment, wherein said disorder is selected from the group consisting of inflammation; fibrosis selected from the group consisting of pulmonary fibrosis, liver fibrosis, kidney fibrosis, ophthalmological fibrosis and fibrosis of the skin and heart; scarring; keloid formation; aberrant scar formation; surgical adhesion; septic shock; cancers selected from the group consisting of carcinomas, sarcomas, leukemias and lymphomas; a metastasizing cancer; autoimmune diseases selected from the group consisting of selpsoriasis, rheumatoid arthritis, Crohn's disease, ulcerative colitis, ankylosing spondylitis, and systemic lupus erythematosus; a metabolic disorder; heart disease; heart failure; pathological angiogenesis; an eye disease selected from age-related macular degeneration and corneal neovascularization; atherosclerosis; a metabolic disease; asthma; Hermansky-Pudlak syndrome; mesothelioma; and a liver disorder.

16. The method of claim 15, wherein the galectin is galectin-3.

17. The method of claim 15, wherein the mammal is a human.

18. The method of claim 15, wherein the pathological angiogenesis is an ocular angiogenesis or a disease or condition associated with ocular angiogenesis.

19. The method of claim 18, wherein the disease or condition associated with ocular angiogenesis is neovascularization related to cancer.

20. The method of claim 15, wherein the metabolic disease is diabetes.

* * * * *